United States Patent
Kim et al.

(10) Patent No.: US 7,781,437 B2
(45) Date of Patent: Aug. 24, 2010

(54) SUBSTITUTED HETEROCYCLIC COMPOUNDS WITH CXCR3 ANTAGONIST ACTIVITY

(75) Inventors: Seong Heon Kim, Livingston, NJ (US);
Bandarpalle B. Shankar, Branchburg, NJ (US); Joseph A. Kozlowski, Princeton, NJ (US); Stuart B. Rosenblum, West Orange, NJ (US); Neng-Yang Shih, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 701 days.

(21) Appl. No.: 11/545,201

(22) Filed: Oct. 10, 2006

(65) Prior Publication Data

US 2007/0082913 A1    Apr. 12, 2007

Related U.S. Application Data

(60) Provisional application No. 60/725,483, filed on Oct. 11, 2005.

(51) Int. Cl.
    *A61K 31/497* (2006.01)
(52) U.S. Cl. .......... 514/252.11; 544/359; 544/405; 544/408; 546/207; 546/245; 548/131; 548/215; 548/250; 548/255; 548/311.1
(58) Field of Classification Search .......... 544/359
    See application file for complete search history.

(56) References Cited

U.S. PATENT DOCUMENTS

| | | | |
|---|---|---|---|
| 6,391,865 B1 | 5/2002 | Baroudy et al. | |
| 7,417,045 B2 | 8/2008 | Anilkumar et al. | |
| 2006/0276448 A1 | 12/2006 | Zeng et al. | |
| 2006/0276457 A1 | 12/2006 | Yu et al. | |
| 2006/0276479 A1 | 12/2006 | Kim et al. | |
| 2006/0276480 A1 | 12/2006 | Wong et al. | |
| 2007/0021611 A1 | 1/2007 | McGuiness et al. | |
| 2007/0054919 A1 | 3/2007 | Rosenblum et al. | |
| 2008/0039474 A1 | 2/2008 | Rosenblum et al. | |
| 2008/0058343 A1 | 3/2008 | Rosenblum et al. | |
| 2008/0292589 A1 | 11/2008 | Anilkumar et al. | |

FOREIGN PATENT DOCUMENTS

| WO | WO 2004/029041 | 4/2004 |
|---|---|---|
| WO | WO 2004/085423 | 10/2004 |
| WO | WO 2004/099144 | 11/2004 |
| WO | WO 2006/088837 | 8/2006 |
| WO | WO 2006/088920 | 8/2006 |
| WO | WO 2006/088921 | 8/2006 |
| WO | WO 2006/091428 | 8/2006 |
| WO | WO2008/079279 | 7/2008 |

OTHER PUBLICATIONS

West, Anthony R., Solid State Chemistry and its Applications, Wiley, New York, 1988, pp. 358 and 365.*
International Search Report for International Application No. PCT/US2006/039404, mailed Mar. 19, 2007—5pgs.
Michael K. C. Wong et al., U.S. Appl. No. 11/354,328; Notice of Allowance—Mail Date May 13, 2009.
Qingbei Zeng et al., U.S. Appl. No. 12/519,970; Preliminary Amendment—Mailed Jun. 18, 2009.
European Patent Communication issued Apr. 8, 2009.

* cited by examiner

*Primary Examiner*—James O Wilson
*Assistant Examiner*—Brian McDowell
(74) *Attorney, Agent, or Firm*—Eric A. Meade; Krishna G. Banerjee

(57) ABSTRACT

The present application discloses a compound, or enantiomers, stereoisomers, rotamers, tautomers, racemates or prodrug of said compound, or pharmaceutically acceptable salts, solvates or esters of said compound, or of said prodrug, said compound having the general structure shown in Formula 1:

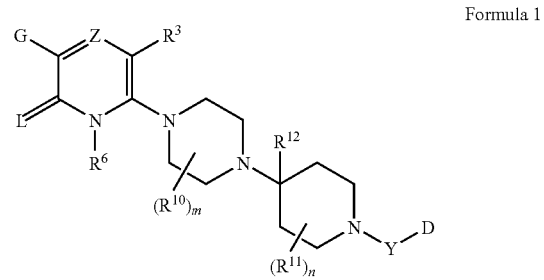

Formula 1 or a pharmaceutically acceptable salt, solvate or ester thereof, wherein the various moieties are defined herein. Also disclosed is a method of treating chemokine mediated diseases, such as, palliative therapy, curative therapy, prophylactic therapy of certain diseases and conditions such as inflammatory diseases (non-limiting example(s) include, psoriasis), autoimmune diseases (non-limiting example(s) include, rheumatoid arthritis, multiple sclerosis), graft rejection (non-limiting example(s) include, allograft rejection, xenograft rejection), infectious diseases (e.g, tuberculoid leprosy), fixed drug eruptions, cutaneous delayed-type hypersensitivity responses, type I diabetes, viral meningitis and tumors using a compound of Formula 1.

15 Claims, No Drawings

SUBSTITUTED HETEROCYCLIC COMPOUNDS WITH CXCR3 ANTAGONIST ACTIVITY

REFERENCE TO PRIORITY APPLICATION

This Application claims the benefit of U.S. Provisional Application Ser. No. 60/725,483, filed Oct. 11, 2005.

FIELD OF THE INVENTION

The present invention relates to substituted heterocyclic compounds with CXCR3 antagonist activity, pharmaceutical compositions containing one or more such antagonists, one or more such antagonists in combination with other compounds with chemokine activity, one or more such antagonists in combination with known immunosuppressive agents, (non-limiting example(s) include Methotrexate, interferon, cyclosporin, FK-506 and FTY720), methods of preparing such antagonists and methods of using such antagonists to modulate CXCR3 activity. This invention also discloses methods of using such CXCR3 antagonists for the treatment (non-limiting examples include palliative, curative and prophylactic therapies) of diseases and conditions where CXCR3 has been implicated. Diseases and conditions where CXCR3 has been implicated include but are not limited to inflammatory conditions (psoriasis and inflammatory bowel disease), autoimmune disease (multiple sclerosis, rheumatoid arthritis), fixed drug eruptions, cutaneous delayed-type hypersensitivity responses, type I diabetes, viral meningitis and tuberculoid leprosy. CXCR3 antagonist activity has also been indicated as a therapy for tumor growth suppression as well as graft rejection (allograft and zenograft rejections for example).

BACKGROUND OF THE INVENTION

Chemokines constitute a family of cytokines that are produced in inflammation and regulate leukocyte recruitment (Baggiolini, M. et al., *Adv. Immunol.*, 55: 97-179 (1994); Springer, T. A., *Annual Rev. Physio.*, 57: 827-872 (1995); and Schall, T. J. and K. B. Bacon, *Curr. Opin. Immunol*, 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e. g., leukotrienes) and respiratory burst, associated with leukocyte activation. Thus, the chemokines are early triggers of the inflammatory response, causing inflammatory mediator release, chemotaxis and extravasation to sites of infection or inflammation.

Chemokines are related in primary structure and share four conserved cysteines, which form disulfide bonds. Based upon this conserved cysteine motif, the family can be divided into distinct branches, including the C—X—C chemokines (α-chemokines) in which the first two conserved cysteines are separated by an intervening residue (e. g., IL-8, IP-10, Mig, I-TAC, PF4, ENA-78, GCP-2, GROα, GROβ, GROδ, NAP-2, NAP-4), and the C—C chemokines (β-chemokines), in which the first two conserved cysteines are adjacent residues (e. g., MIP-1α, MIP-1β, RANTES, MCP-1, MCP-2, MCP-3, I-309) (Baggiolini, M. and Dahinden, C. A., *Immunology Today*, 15: 127-133 (1994)). Most CXC-chemokines attract neutrophil leukocytes. For example, the CXC-chemokines interleukin-8 (IL-8), GRO alpha (GROα), and neutrophil-activating peptide 2 (NAP-2) are potent chemoattractants and activators of neutrophils. The CXC-chemokines designated Mig (monokine induced by gamma interferon) and IP-10 (interferon-gamma inducible 10 kDa protein) are particularly active in inducing chemotaxis of activated peripheral blood lymphocytes.

CC-chemokines are generally less selective and can attract a variety of leukocyte cell types, including monocytes, eosinophils, basophils, T lymphocytes and natural killer cells. CC-chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

A chemokine receptor that binds the CXC-chemokines IP-10 and Mig has been cloned, characterized (Loetscher, M. et al., *J. Exp. Med.*, 184: 963-969 (1996)) and designated CXCR3. CXCR3 is a G-protein coupled receptor with seven transmembrane-spanning domains and has been shown to be restrictively expressed in activated T cells, preferentially human Th1 cells. On binding of the appropriate ligand, chemokine receptors transduce an intracellular signal through the associated G-protein resulting in a rapid increase in intracellular calcium concentration.

The CXCR3 receptor mediates $Ca^{2+}$ (calcium ion) mobilization and chemotaxis in response to IP-10 and Mig. CXCR3 expressing cells show no significant response to the CXC-chemokines IL-8, GROα, NAP-2, GCP-2 (granulocyte chemotactic protein-2), ENA78 (epithelial-derived neutrophil-activating peptide 78), PF4 (platelet factor 4), or the CC-chemokines MCP-1, MCP-2, MCP-3, MCP-4, MIP-Iα, MIP-1β, RANTES, I309, eotaxin or lymphotactin. Moreover, a third ligand for CXCR3, I-TAC (Interferon-inducible T cell Alpha Chemoattractant), has also been found to bind to the receptor with high affinity and mediate functional responses (Cole, K. E. et al., *J. Exp. Med.*, 187: 2009-2021 (1998)).

The restricted expression of human CXCR3 in activated T lymphocytes and the ligand selectivity of CXCR3 are noteworthy. The human receptor is highly expressed in IL-2 activated T lymphocytes, but was not detected in resting T lymphocytes, monocytes or granulocytes (Qin, S. et al., *J. Clin. Invest.*, 101: 746-754 (1998)). Additional studies of receptor distribution indicate that it is mostly CD3$^+$ cells that express CXCR3, including cells which are CD95$^+$, CD45RO$^+$, and CD45RA$^{low}$, a phenotype consistent with previous activation, although a proportion of CD20$^+$ (B) cells and CD56$^+$ (NK) cells also express this receptor. The selective expression in activated T lymphocytes is of interest, because other receptors for chemokines which have been reported to attract lymphocytes (e. g., MCP-1, MCP-2, MCP-3, MIP-1α, MIP-1β, RANTES) are also expressed by granulocytes, such as neutrophils, eosinophils, and basophils, as well as monocytes. These results suggest that the CXCR3 receptor is involved in the selective recruitment of effector T cells.

CXCR3 recognizes unusual CXC-chemokines, designated IP-10, Mig and I-TAC. Although these belong to the CXC-subfamily, in contrast to IL-8 and other CXC-chemokines which are potent chemoattractants for neutrophils, the primary targets of IP-10, Mig and I-TAC are lymphocytes, particularly effector cells such as activated or stimulated T lymphocytes and natural killer (NK) cells (Taub, D. D. et al., *J*

Exp. Med., 177:18090-1814 (1993); Taub, D. D. et al., J. Immunol., 155: 3877-3888 (1995); Cole, K. E. et al., J. Exp. Med., 187: 2009-2021 (1998)). (NK cells are large granular lymphocytes, which lack a specific T cell receptor for antigen recognition, but possess cytolytic activity against cells such as tumor cells and virally infected cells.) Consistently, IP-10, Mig and I-TAC lack the ELR motif, an essential binding epitope in those CXC-chemokines that efficiently induce neutrophil chemotaxis (Clark-Lewis, I. et al., J. Biol. Chem. 266: 23128-23134 (1991); Hebert, C. A. et al., J. Biol. Chem., 266: 18989-18994 (1991); and Clark-Lewis, 1. et al., Proc. Natl. Acad. Sci. USA, 90: 3574-3577 (1993)). In addition, both recombinant human Mig and recombinant human IP-10 have been reported to induce calcium flux in tumor infiltrating lymphocytes (TIL) (Liao, F. et al., J Exp. Med, 182: 1301-1314 (1995)). While IP-10 has been reported to induce chemotaxis of monocytes in vitro (Taub, D. D. et al., J. Exp. Med., 177: 1809-1814 (1993), the receptor responsible has not been identified), human Mig and I-TAC appear highly selective, and do not show such an effect (Liao, F. et al., J. Exp. Med., 182: 1301-1314 (1995); Cole, K. E. et al., J. Exp. Med., 187: 2009-2021 (1998)). IP-10 expression is induced in a variety of tissues in inflammatory conditions such as psoriasis, fixed drug eruptions, cutaneous delayed-type hypersensitivity responses and tuberculoid leprosy as well as tumors and in animal model studies, for example, experimental glomerulonephritis, and experimental allergic encephalomyelitis. IP-10 has a potent in vivo antitumor effect that is T cell dependent, is reported to be an inhibitor of angiogenesis in vivo and can induce chemotaxis and degranulation of NK cells in vitro, suggesting a role as a mediator of NK cell recruitment and degranulation (in tumor cell destruction, for example) (Luster, A. D. and P. Leder, J. Exp. Med., 178: 1057-1065 (1993); Luster, A. D. et al., J Exp. Med. 182: 219-231 (1995); Angiolillo, A. L. et al., J. Exp. Med., 182: 155-162 (1995); Taub, D. D. et al., J. Immunol., 155: 3877-3888 (1995)). The expression patterns of IP-10, Mig and I-TAC are also distinct from that of other CXC chemokines in that expression of each is induced by interferon-gamma (IFNδ), while the expression of IL-8 is down-regulated by IFNδ (Luster, A. D. et al., Nature, 315: 672-676 (1985); Farber, J. M., Proc. Natl. Acad. Sci. USA, 87: 5238-5242 (1990); Farber, J. M., Biochem. Biophys. Res. Commun., 192 (1): 223-230 (1993), Liao, F. et al., J. Exp. Med., 182: 1301-1314 (1995); Seitz, M. et al., J. Clin. Invest., 87: 463-469 (1991); Galy, A. H. M. and H. Spits, J. Immunol., 147: 3823-3830 (1991); Cole, K. E. et al., J. Exp. Med., 187: 2009-2021 (1998)).

Chemokines are recognized as the long-sought mediators for the recruitment of lymphocytes. Several CC-chemokines were found to elicit lymphocyte chemotaxis (Loetscher, P. et al., FASEB J., 8: 1055-1060 (1994)), however, they are also active on granulocytes and monocytes (Uguccioni, M. et al., Eur. J. Immunol., 25: 64-68 (1995); Baggiolini, M. and C. A. Dahinden, Immunol. Today, 15: 127-133 (1994)). The situation is different for IP-10, Mig and I-TAC, which are selective in their action on lymphocytes, including activated T lymphocytes and NK cells, and which bind CXCR3, a receptor which does not recognize numerous other chemokines and which displays a selective pattern of expression.

In view of these observations, it is reasonable to conclude that the formation of the characteristic infiltrates in inflammatory lesions, such as, for example, delayed-type hypersensitivity lesions, sites of viral infection and certain tumors is a process mediated via CXCR3 and regulated by CXCR3 expression. Lymphocytes, particularly T lymphocytes, bearing a CXCR3 receptor as a result of activation can be recruited into inflammatory lesions, sites of infection and/or tumors by IP-10, Mig and/or I-TAC, which can be induced locally by interferon-gamma. Thus, CXCR3 plays a role in the selective recruitment of lymphocytes, particularly effector cells such as activated or stimulated T lymphocytes. Accordingly, activated and effector T cells have been implicated in a number of disease states such as graft-rejection, inflammation, rheumatoid arthritis, multiple sclerosis, inflammatory bowel disease and psoriasis. Thus, CXCR3 represents a promising target for the development of novel therapeutics.

Reference is made to EP1048652A1 (published Nov. 2, 2000), which refers to aromatic compounds having cyclic amino or salts thereof, which specifically inhibit FXa, exert a potent anticoagulant effect and thus are useful as medicinal compositions.

Reference is made to PCT Publication No. WO 93/10091 (Applicant: Glaxo Group Limited, Published May 27, 1993) which discloses piperidine acetic acid derivatives as inhibitors of fibrinogen-dependent blood platelet aggregation having the formula:

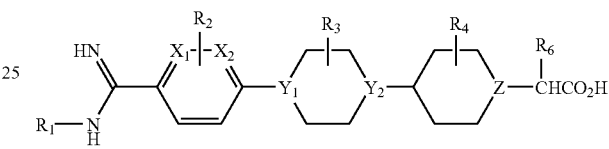

An illustrative compound of that series is:

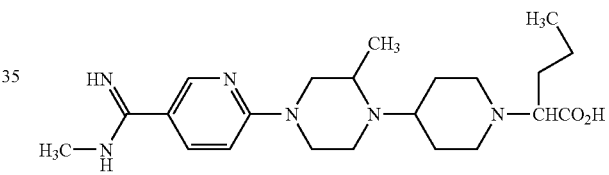

Reference is also made to PCT Publication No. WO 99/20606 (Applicant: J. Uriach & CIA. S. A., Published Apr. 29, 1999) which discloses piperazines as platelet aggregation inhibitors having the formula:

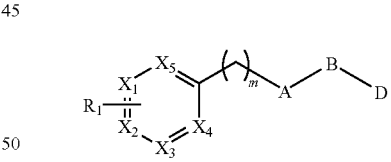

Reference is also made to U.S. patent application Ser. No. US 2002/0018776 A1 (Applicant: Hancock, et al. Published Feb. 14, 2002) which discloses methods of treating graft rejection.

Reference is also made to PCT Publication No. WO 03/098185 A2 (Applicant: Renovar, Inc., Published Nov. 27, 2003) which discloses methods of diagnosing and predicting organ transplant rejection by detection of chemokines, for example, CXCR3 and CCL chemokines in urine.

Reference is also made to PCT Publication No. WO 03/082335 A1 (Applicant: Sumitomo Pharmaceuticals Co. Ltd., Published Oct. 9, 2003) which discloses methods of screening a CXCR3 ligand and methods of diagnosing type 2 diabetes by detecting the expression dose of a CXCR3 ligand in a biological sample.

Reference is also made to PCT Publication No. WO 02/085861 (Applicant: Millennium Pharmaceuticals, Inc. Published Oct. 31, 2002) which discloses imidazolidine compounds and their use as CXCR3 antagonists having the formula:

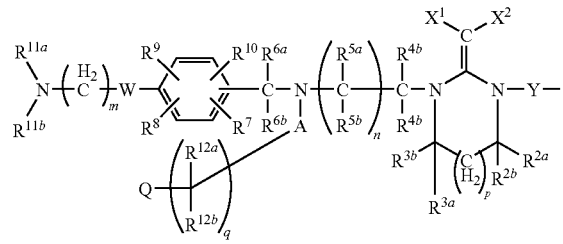

An illustrative compound of that series is:

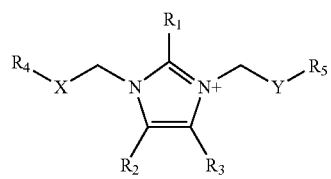

Reference is also made to PCT Publication No. WO 03/101970 (Applicant: Smithkline Beecham Corporation, Published Dec. 11, 2003) which discloses imidazolium compounds and their use as CXCR3 antagonists having the formula:

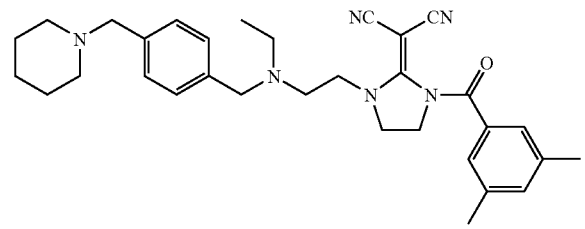

An illustrative example of that series is:

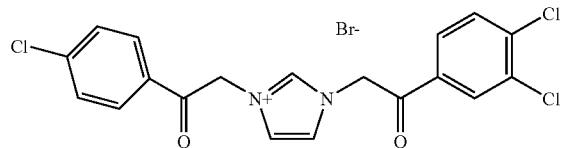

Reference is also made to U.S. patent application Ser. No. US 2003/0055054 A1 (Applicant: Medina et al, Published Mar. 20, 2003) and related patent U.S. Pat. No. 6,794,379 B2 ((Applicant: Medina et al, Published Sep. 21, 2004) which discloses compounds with CXCR3 activity having the formula:

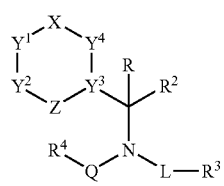

An illustrative compound of that series is:

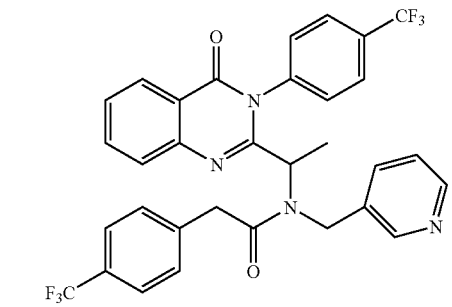

Reference is also made to U.S. Pat. No. 6,124,319 (Applicant: MacCoss et al., issued Sep. 6, 2000) which discloses compounds useful as chemokine receptor modulators having the formula:

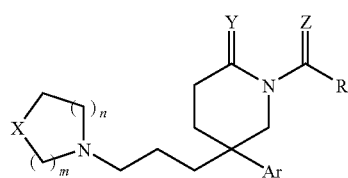

Reference is also made to PCT Publication WO 03/070242 A1 (Applicant: CELLTECH R&D limited, Published Aug. 28, 2003) which discloses compounds useful as "chemokine receptor inhibitors for the treatment of inflammatory diseases" having the formula:

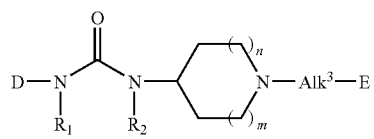

Reference is also made to PCT Publication WO 04/074287 A1, WO 04/074273 A1, WO 04/74278 (Applicant: AstraZeneca R & D Published Feb. 19, 2004) which discloses pyridine derivatives, processes for their preparation and their use in the modulation of autoimmune disease having the formula:

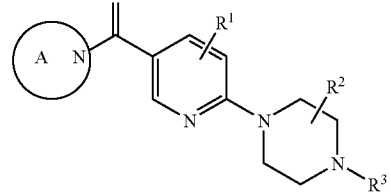

where $R^3$ is phenyl, or a 5- or 6-membered aromatic ring with 1 or more nitrogen atoms.

There is a need for compounds that are capable of modulating CXCR3 activity. For example, there is a need for new treatments and therapies for diseases and conditions associated with CXCR3 such as inflammatory conditions (psoriasis and inflammatory bowel disease), autoimmune disease (multiple sclerosis, rheumatoid arthritis) and graft rejection (allograft and zenograft rejections for example) as well as infectious diseases, cancers and tumors, fixed drug eruptions, cutaneous delayed-type hypersensitivity responses, type I diabetes, viral meningitis and tuberculoid leprosy.

There is a need for methods of treatment or prevention or amelioration of one or more symptoms of diseases and conditions associated with CXCR3. There is a need for methods for modulating CXCR3 activity using the compounds provided herein.

SUMMARY OF THE INVENTION

In its many embodiments, the present invention discloses a compound having the general structure shown in Formula 1:

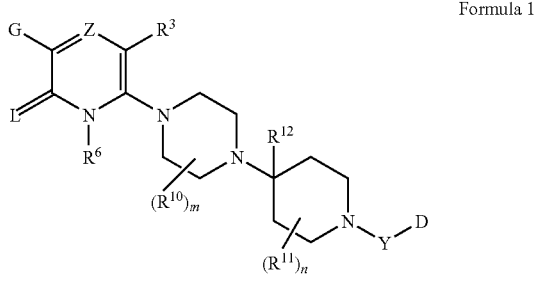

Formula 1 or a pharmaceutically acceptable salt, solvate or ester thereof, wherein:

G is selected from the group consisting of H, hydroxyl, alkoxy, $R^2R^1N-$, $R^2R^1X-C(R^{14})(R^{15})-$, and a 5-membered heteroaryl or heterocyclenyl ring containing at least one —C=N— moiety as part of said heteroaryl or heterocyclenyl ring, said heteroaryl or heterocyclenyl ring optionally additionally containing one or more moieties selected from the group consisting of N, N(→O), O, S, S(O) and S(O)$_2$ on the ring, which moieties can be the same or different, each being independently selected, further wherein said heteroaryl or heterocyclenyl ring can be either (i) unsubstituted, or (ii) optionally independently substituted on one or more ring carbon atoms with one or more $R^9$ substituents, or on one or more ring nitrogen atoms with one or more $R^8$ substituents, wherein said $R^8$ and $R^9$ substituents can be the same or different;

L is O or S;

Z is N or $CR^4$;

$R^1$ and $R^2$ are independently absent or present, and if present each is independently selected from the group consisting of H, alkyl, alkoxy, alkenyl, carbonyl, cycloalkyl, cycloalkenyl, alkylaryl, arylalkyl, aryl, amino, alkylamino, amidinyl, carboxamido, cyano, hydroxyl, urea, —N=CH, =NCN, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —C(=S)N(H)alkyl, —N(H)—S(O)$_2$-alkyl, —N(H)C(=O)N(H)-alkyl, —S(O)$_2$alkyl, —S(O)$_2$N(H)alkyl, —S(O)$_2$N(alkyl)$_2$, —S(O)$_2$aryl, —C(=S)N(H)cycloalkyl, —C(=O)N(H)NH$_2$, —C(=O)alkyl, -heteroaryl, heterocyclyl, and heterocyclenyl; or alternatively when X is N, the N taken together with the $R^1$ and $R^2$ forms a heterocyl, heteroaryl or —N=C(NH$_2$)$_2$;

$R^3$ and $R^4$ moieties can be the same or different, each being independently selected from the group consisting of H, alkyl, alkylaryl, aralkyl, —CN, CF$_3$, haloalkyl, cycloalkyl, halogen, hydroxyalkyl, —N=CH—(R$^{31}$), —C(=O)N(R$^{30}$)$_2$, —N(R$^{30}$)$_2$, —OR$^{30}$, —SO$_2$(R$^{31}$), —N(R$^{30}$)C(=O)N(R$^{30}$)$_2$ and —N(R$^{30}$)C(=O)R$^{31}$;

$R^6$ is selected from the group consisting of H, alkyl, arylalkyl, and alkylaryl;

X is selected from the group consisting of N, O, alkyl, cycloalkyl, heteroaryl, heterocyclyl, and heterocyclenyl;

the $R^8$ moieties can be the same or different, each being independently selected from the group consisting of H, alkyl, alkenyl, alkylaryl, arylalkyl, cycloalkyl, aryl, heteroaryl, heterocyclyl, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, and —(CH$_2$)$_q$SO$_2$NHR$^{31}$;

the $R^9$ moieties can be the same or different, each being independently selected from the group consisting of H, alkyl, alkenyl, alkylaryl, arylalkyl, alkoxy, amidinyl, aryl, cycloalkyl, cyano, heteroaryl, heterocyclyl, hydroxyl, —C(=O)N(R$^{30}$)$_2$, —C(=S)N(R$^{30}$)$_2$, —C(=O)alkyl, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, —N(R$^{30}$)$_2$, —N(R$^{30}$)S(O$_2$)R$^{31}$, —N(R$^{30}$)C(=O)N(R$^{30}$)$_2$, —OR$^{30}$, —SO$_2$(R$^{31}$), —SO$_2$N(R$^{30}$)$_2$, =O and =S;

the $R^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyalkyl, —C(=O)N(R$^{30}$)$_2$, —(CH$_2$)$_q$OH, —(CH$_2$)$_q$OR$^{31}$, —OR$^{30}$, halogen, =O, and —C(=O)R$^{31}$;

the $R^{11}$ moieties can be the same or different, each being independently selected from the group consisting of H, alkyl, cycloalkyl, aryl, heteroaryl, heterocyclyl, heterocyclenyl, alkylaryl, arylalkyl, carboxamide, CO$_2$H, —(CH$_2$)$_q$OH, —(CH$_2$)$_q$OR$^{31}$, —OR$^{30}$, halogen, =O, and —C(=O)R$^{31}$;

$R^{12}$ moieties can be the same or different, each being independently selected from the group consisting of H, alkyl, —CN, —C(=O)N(R$^{30}$)$_2$, —(CH$_2$)$_q$OH, —(CH$_2$)$_q$OR$^{31}$ and —S(O$_2$)R$^{31}$;

ring D is a five to nine membered cycloalkyl, cycloalkenyl, aryl, heteroaryl, heterocyclenyl or heterocyclyl ring having 0-4 heteroatoms independently selected from O, S or N, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$; or alternatively two $R^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 $R^{21}$ moieties;

the $R^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, $-(CH_2)_qOH$, $-(CH_2)_qOR^{31}$, $-(CH_2)_q NH_2$, $-(CH_2)_qNHR^{31}$, $-(CH_2)_qC(=O)NHR^{31}$, $-(CH_2)_q SO_2R^{31}$, $-(CH_2)_qNSO_2R^{31}$, $-(CH_2)_qSO_2NHR^{31}$, -alkynylC$(R^{31})_2OR^{31}$, $-C(=O)R^{30}$, $-C(=O)N(R^{30})_2$, $-C(=NR^{30})NHR^{30}$, $-C(=NOH)N(R^{30})_2$, $-C(=NOR^{31})N(R^{30})_2$, $-C(=O)OR^{30}$, $-N(R^{30})_2$, $-N(R^{30})C(=O)R^{31}$, $-NHC(=O)N(R^{30})_2$, $-N(R^{30})C(=O)OR^{31}$, $-N(R^{30})C(=NCN)N(R^{30})_2$, $-N(R^{30})C(=O)N(R^{30})SO_2(R^{31})$, $-N(R^{30})C(=O)N(R^{30})_2$, $-N(R^{30})SO_2(R^{31})$, $-N(R^{30})S(O)_2N(R^{30})_2$, $-OR^{30}$, $-OC(=O)N(R^{30})_2$, $-SR^{30}$, $-SO_2N(R^{30})_2$, $-SO_2(R^{31})$, $-OSO_2(R^{31})$, and $-OSi(R^{30})_3$;

Y is selected from the group consisting of $-(CR^{13}R^{13})_r-$, $-CHR^{13}C(=O)-$, $-(CHR^{13})_rO-$, $-(CHR^{13})_rN(R^{30})-$, $-C(=O)-$, $-C(=NR^{30})-$, $-C(=N-OR^{30})-$, $-CH(C(=O)NHR^{30})-$, CH-heteroaryl-, $-C(R^{13}R^{13})_rC(R^{13})=C(R^{13})-$, $-(CHR^{13})_rC(=O)-$ and $-(CHR^{13})_rN(H)C(=O)-$; or alternatively Y is cycloalkyl, heterocyclenyl, or heterocyclyl wherein the cycloalkyl, heterocyclenyl, or heterocyclyl is fused with ring D;

the $R^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, $-CN$, $-CO_2H$, $-C(=O)R^{30}$, $-C(=O)N(R^3)_2$, $-(CHR^{30})_qOH$, $-(CHR^{30})_qOR^{31}$, $-(CHR^{30})_qNH_2$, $-(CH\ R^{30})_qNHR^{31}$, $-(CH_2)_qC(=O)NHR^3$, $-(CH_2)_qSO_2R^{31}$, $-(CH_2)_qNSO_2R^{31}$, $-(CH_2)_q SO_2NHR^{31}$, $-NH_2$, $-N(R^{30})_2$, $-N(R^{30})C(=O)N(R^{30})_2$, $-N(R^{30})SO_2(R^{31})$, $-OH$, $OR^{30}$, $-SO_2N(R^{30})_2$, and $-SO_2(R^{31})$;

$R^{14}$ and $R^{15}$ are the same or different, each being independently selected from the group consisting of H, alkyl, alkylaryl, heteroaryl, hydroxyl, $-CN$, alkoxy, alkylamino, $-N(H)S(O)_2$alkyl and $-N(H)C(=O)N(H)$alkyl; or alternatively $R^{14}$ and $R^{15}$ taken together is =O, =S, =NH, =N(alkyl), =N(Oalkyl), =N(OH) or cycloalkyl;

the $R^{30}$ moieties can be the same or different, each being independently selected from the group consisting of H, alkyl, alkylaryl, aryl, aralkyl, cycloalkyl, $-(CH_2)_qOH$, $-(CH_2)_q Oalkyl$, $-(CH_2)_qOalkylaryl$, $-(CH_2)_qOaryl$, $-(CH_2)_q Oaralkyl$, $-(CH_2)_qOcycloalkyl$, $-(CH_2)_qNH_2$, $-(CH_2)_q NHalkyl$, $-(CH_2)_qN(alkyl)_2$, $-(CH_2)_qNHalkylaryl$, $-(CH_2)_qNHaryl$, $-(CH_2)_qNHaralkyl$, $-(CH_2)_qNHcycloalkyl$, $-(CH_2)_qC(=O)NHalkyl$, $-(CH_2)_qC(=O)N(alkyl)_2$, $-(CH_2)_qC(=O)NHalkylaryl$, $-(CH_2)_qC(=O)NHaryl$, $-(CH_2)_qC(=O)NHaralkyl$, $-(CH_2)_qC(=O)NHcycloalkyl$, $-(CH_2)_qSO_2alkyl$, $-(CH_2)_qSO_2alkylaryl$, $-(CH_2)_qSO_2aryl$, $-(CH_2)_qSO_2aralkyl$, $-(CH_2)_q SO_2cycloalkyl$, $-(CH_2)_qNSO_2alkyl$, $-(CH_2)_q NSO_2alkylaryl$, $-(CH_2)_qNSO_2aryl$, $-(CH_2)_q NSO_2aralkyl$, $-(CH_2)_qNSO_2cycloalkyl$, $-(CH_2)_q SO_2NHalkyl$, $-(CH_2)_q SO_2NHalkylaryl$, $-(CH_2)_q SO_2NHaryl$, $-(CH_2)_q SO_2NHaralkyl$, $-(CH_2)_q SO_2NHcycloalkyl$, heterocyclenyl, heterocyclyl, and heteroaryl;

the $R^{31}$ moieties can be the same or different, each being independently selected from the group consisting of alkyl, alkylaryl, aryl, aralkyl, cycloalkyl, $-(CH_2)_qOH$, $-(CH_2)_q Oalkyl$, $-(CH_2)_qOalkylaryl$, $-(CH_2)_qOaryl$, $-(CH_2)_q Oaralkyl$, $-(CH_2)_qOcycloalkyl$, $-(CH_2)_qNH_2$, $-(CH_2)_q NHalkyl$, $-(CH_2)_qN(alkyl)_2$, $-(CH_2)_qNHalkylaryl$, $-(CH_2)_qNHaryl$, $-(CH_2)_qNHaralkyl$, $-(CH_2)_qNHcycloalkyl$, $-(CH_2)_qC(=O)NHalkyl$, $-(CH_2)_qC(=O)N(alkyl)_2$, $-(CH_2)_qC(=O)NHalkylaryl$, $-(CH_2)_qC(=O)NHaryl$, $-(CH_2)_qC(=O)NHaralkyl$, $-(CH_2)_qC(=O)NHcycloalkyl$, $-(CH_2)_qSO_2alkyl$, $-(CH_2)_qSO_2alkylaryl$, $-(CH_2)_qSO_2aryl$, $-(CH_2)_qSO_2aralkyl$, $-(CH_2)_q SO_2cycloalkyl$, $-(CH_2)_qNSO_2alkyl$, $-(CH_2)_q NSO_2alkylaryl$, $-(CH_2)_qNSO_2aryl$, $-(CH_2)_q NSO_2aralkyl$, $-(CH_2)_qNSO_2cycloalkyl$, $-(CH_2)_q SO_2NHalkyl$, $-(CH_2)_q SO_2NHalkylaryl$, $-(CH_2)_q SO_2NHaryl$, $-(CH_2)_q SO_2NHaralkyl$, $-(CH_2)_q SO_2NHcycloalkyl$, heterocyclenyl, heterocyclyl, and hetroaryl;

m is 0 to 4;

n is 0 to 4;

each q can be the same or different, each being independently selected from 1 to 5; and r is 1 to 4;

with the proviso that there are no two adjacent double bonds in any ring, and that when a nitrogen is substituted by two alkyl groups, said two alkyl groups may be optionally joined to each other to form a ring.

Where G represents "a 5-membered heteroaryl or heterocyclenyl ring containing at least one $-C=N-$ moiety" refers to G representing, in a non-limiting manner, moieties such as dihydroimidazole, imidazole, dihydrooxazole, oxazole, dihydrooxadiazole, oxadiazole, dihydrothiazole, thiazole, triazole, tetrazole and the like. These moieties may be optionally substituted on the ring carbon(s) with one or more $R^9$ groups as stated above, or on the ring nitrogen(s) with one or more $R^8$ groups as stated above.

A further feature of the invention is a pharmaceutical composition containing as active ingredient at least one compound of Formula 1 together with at least one pharmaceutically acceptable carrier or excipient.

The invention provides methods of preparing compounds of Formula 1, as well as methods for treating diseases, for example, treatment (e.g., palliative therapy, curative therapy, prophylactic therapy) of certain diseases and conditions e.g., inflammatory diseases (e.g., psoriasis), autoimmune diseases (e.g., rheumatoid arthritis, multiple sclerosis), graft rejection (e.g., allograft rejection, xenograft rejection), infectious diseases and tumors. The invention provides a method of treating a CXCR3 chemokine mediated disease in a patient in need of such treatment comprising administering to the patient a therapeutically effective amount of at least one compound of Formula 1, or a pharmaceutically acceptable salt, solvate or ester thereof.

The invention provides methods of treating diseases, for example, treatment (e.g., palliative therapy, curative therapy, prophylactic therapy) of certain diseases and conditions such as inflammatory diseases (e.g., psoriasis), autoimmune diseases (e.g., rheumatoid arthritis, multiple sclerosis), graft rejection (e.g., allograft rejection, xenograft rejection), infectious diseases as well as cancers and tumors, fixed drug eruptions, cutaneous delayed-type hypersensitivity responses, type I diabetes, viral meningitis and tuberculoid leprosy comprising administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives; steroids; PDE IV inhibitors, anti-TNF-α compounds, MMP inhibitors, glucocorticoids, other chemokine inhibitors such as CCR2 and CCR5, CB2-selective inhibitors, and other classes of compounds indicated for the treatment of rheumatoid arthritis.

The invention also provides a method of modulating (inhibiting or promoting) an inflammatory response in an individual in need of such therapy. The method comprises administering a therapeutically effective amount of a compound (e.g., small organic molecule) which inhibits or promotes mammalian CXCR3 function in an individual in need thereof. Also disclosed is a method of inhibiting or blocking T-cell mediated chemotaxis in a patient in need of such treatment comprising administering to the patient a therapeutically effective amount of a compound of Formula 1 or a pharmaceutically acceptable salt, solvate or ester thereof.

Also disclosed is a method of treating inflammatory bowel disease in a patient in need of such treatment comprising administering to the patient a therapeutically effective amount of at least one compound of Formula 1, or a pharmaceutically acceptable salt, solvate or ester thereof.

Also disclosed is a method of treating graft rejection in a patient in need of such treatment comprising administering to the patient a therapeutically effective amount of at least one compound of Formula 1, or a pharmaceutically acceptable salt, solvate or ester thereof.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: glatiramer acetate, glucocorticoids, methotrexate, azothioprine, mitoxantrone, and CB2-selective inhibitors.

Also disclosed is a method of treating rheumatoid arthritis in a patient in need of such treatment the method comprising administering to the patient a therapeutically effective amount of: (a) at least one compound of Formula 1, or a pharmaceutically acceptable salt, solvate or ester thereof concurrently or sequentially with (b) at least one compound selected from the group consisting of: COX-2 inhibitors, COX-1 inhibitors, immunosuppressives, steroids, PDE IV inhibitors, anti-TNF-α compounds, MMP inhibitors, glucocorticoids, chemokine inhibitors, CB2-selective inhibitors, caspase (ICE) inhibitors and other classes of compounds indicated for the treatment of rheumatoid arthritis.

Also disclosed is a method of treating psoriasis in a patient in need of such treatment the method comprising administering to the patient a therapeutically effective amount of: a) at least one compound of Formula 1, or a pharmaceutically acceptable salt, solvate or ester thereof concurrently or sequentially with (b) at least one compound selected from the group consisting of: immunosuppressives, steroids, and anti-TNF-α compounds.

The invention also provides a method of treating a disease selected from the group consisting of: inflammatory disease, rheumatoid arthritis, multiple sclerosis, inflammatory bowel disease, graft rejection and psoriasis in a patient in need of such treatment such method comprising administering to the patient an effective amount of at least one compound of Formula 1, or a pharmaceutically acceptable salt, solvate or ester thereof.

The invention also provides a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, type I diabetes, viral meningitis, tuberculoid leprosy as well as tumors and cancers in a patient in need of such treatment, such method comprising administering to the patient an effective amount of (a) at least one compound according to claim 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives; steroids; PDE IV inhibitors, anti-TNF-α compounds, MMP inhibitors, glucocorticoids, chemokine inhibitors, CB2-selective inhibitors, biological response modifiers; anti-inflammatory agents and therapeutics.

DETAILED DESCRIPTION OF THE INVENTION

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

As used above, and throughout the specification, the following terms, unless otherwise indicated, shall be understood to have the following meanings:

"Acyl" means an H—C(=O)—, alkyl-C(=O)—, alkenyl-C(=O)—, alkynyl-C(=O)—, cycloalkyl-C(=O)—, cycloalkenyl-C(=O)—, or cycloalkynyl-C(=O)— group in which the various groups are as previously described. The bond to the parent moiety is through the carbonyl carbon atom. Preferred acyls contain a lower alkyl. Non-limiting examples of suitable acyl groups include formyl, acetyl, propanoyl, 2-methylpropanoyl, butanoyl and cyclohexanoyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The alkenyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, amino, aminosulfonyl, halo, carboxyl, carboxyalkyl (non-limiting example(s) include ester), alkoxycarbonyl, hydroxyalkyl, carbonyl (non-limiting example(s) include ketone), —C(=O)heterocyclyl, formyl (non-limiting example(s) include aldehyde), carboxamido (i.e amido, —C(=O)NH$_2$), —C(=O)N(alkyl)$_2$, —C(=O)NH(alkyl), —C(=O)N(cycloalkyl)$_2$, —C(=O)NH(cycloalkyl), —NHC(=O)alkyl, urea (e.g —NH(C=O)NH$_2$, —NH(C=O)NH(alkyl), —NH(C=O)NH(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e —CO$_2$NH$_2$), NHC(=O)Oalkyl, —CO$_2$N(alkyl)$_2$, —NHC(=O))NH—S(O)$_2$alkyl, —NHC(=O)N(alkyl)$_2$—S(O)$_2$alkyl, —NH—S(O)$_2$alkyl, —NH—S(O)$_2$heteroaryl, —N(alkyl)—S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, alkylthiocarboxy, —S(O)$_2$alkyl, —S(O)$_2$aryl, —OS(O)$_2$alkyl, —OS(O)$_2$aryl, sulfonyl urea (non-limiting example(s) include NHC(=S)

NHalkyl). Non-limiting examples of suitable alkenyl groups include ethenyl, propenyl, n-butenyl, 3-methylbut-2-enyl, n-pentenyl, octenyl and decenyl.

"Alkyl" means an aliphatic hydrocarbon group which may be straight or branched or a combination thereof, and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), alkoxycarbonyl, hydroxyalkyl, carbonyl (non-limiting example(s) include ketone), —C(=O)heterocyclyl, formyl, carboxamido (i.e amido, —C(=O)NH$_2$, —C(=O)N(alkyl)$_2$, —C(=O)NH(alkyl), —C(=O)N(cycloalkyl)$_2$, —C(=O)NH(cycloalkyl)), —NHC(=O)alkyl, amidinyl, hydrazidyl, hydroxamate, —NHC(=O)H, —NHC(=O)alkyl, urea (e.g —NH(C=O)NH$_2$, —NH(C=O)NH(alkyl), —NH(C=O)NH(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e —CO$_2$NH$_2$), —NHC(=O)Oalkyl, —CO$_2$N(alkyl)$_2$, —NHC(=O)NH—S(O)$_2$alkyl, —NHC(=O)N(alkyl)-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, thio, alkylthio, alkylthiocarboxy, —S(O)alkyl, —S(O)$_2$alkyl, —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkylheteroaryl" means an alkyl-heteroaryl- group wherein the alkyl is as previously described and the bond to the parent moiety is through the heteroaryl group.

"Alkylamino" means an —NH$_2$ or —NH$_3^+$ group in which one or more of the hydrogen atoms on the nitrogen is replaced by an alkyl group as defined above. The bond to the parent is through the nitrogen.

"Alkylaryl" means an alkyl-aryl- group in which the alkyl and aryl are as described herein. Preferred alkylaryls comprise a lower alkyl group. Non-limiting examples of suitable alkylaryl groups include o-tolyl, p-tolyl and xylyl. The bond to the parent moiety is through the aryl.

"Alkylthio" means an alkyl-S— group in which the alkyl group is as described herein. Non-limiting examples of suitable alkylthio groups include methylthio, ethylthio, i-propylthio and heptylthio. The bond to the parent moiety is through the sulfur.

"Alkylthiocarboxy" means an alkyl-S—C(=O)O— group. Preferred groups are those in which the alkyl group is lower alkyl. The bond to the parent moiety is through the carboxy.

"Alkylsulfonyl" means an alkyl-S(O)$_2$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, alkoxyl, aryl, aryloxy, cycloalkyl, cycloalkenyl, cyano, heteroaryl, heterocyclyl, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, alkoxycarbonyl, hydroxyalkyl, carbonyl (non-limiting example(s) include ketone), —C(=O)heterocyclyl, carboxamido (i.e amido, —C(=O)NH$_2$), —C(=O)N(alkyl)$_2$, —C(=O)NH(alkyl), —C(=O)N(cycloalkyl)$_2$, —C(=O)NH(cycloalkyl), alkylC(=O)NH—, —NHC(=O)alkyl, urea (e.g —NH(C=O)NH$_2$) —NH(C=O)NH(alkyl), —NH(C=O)NH(alkyl)$_2$, —NH(C=O)NH(heteroaryl), —NH(C=O)NH(heterocyclyl), —S(O)$_2$alkyl, and —S(O)$_2$aryl.—

"Alkoxy" means an alkyl-O— group in which the alkyl group is as previously described. Non-limiting examples of suitable alkoxy groups include methoxy, ethoxy, n-propoxy, isopropoxy, n-butoxy, heptoxy and methylhydroxy. The bond to the parent moiety is through the ether oxygen.

"Alkoxycarbonyl" means an alkyl-O—C(=O)— group. Non-limiting examples of suitable alkoxycarbonyl groups include methoxycarbonyl and ethoxycarbonyl. The bond to the parent moiety is through the carbonyl.

"Aminoalkyl" means an amine-alkyl- group in which alkyl is as previously defined. Preferred aminoalkyls contain lower alkyl. Non-limiting examples of suitable aminoalkyl groups include aminomethyl and 2-Dimethlylamino-2-ethyl. The bond to the parent moiety is through the alkyl.

"Amidinyl" means —C(=NR)NHR group. The R groups are defined as H, alkyl, alkylaryl, heteroaryl, hydroxyl, alkoxy, amino, ester, —NHSO$_2$alkyl, —NHSO$_2$Aryl, —NHC(=O)NHalkyl, and —NHalkyl. The bond to the parent moiety is through the carbon.

"Aralkyl" or "arylalkyl" means an aryl-alkyl- group in which the aryl and alkyl are as previously described. Preferred aralkyls comprise a lower alkyl group attached to the aryl group. Non-limiting examples of suitable aralkyl groups include benzyl, 2-phenethyl and naphthalenylmethyl. The bond to the parent moiety is through the alkyl.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkylthio" means an aralkyl-S— group in which the aralkyl group is as previously described. Non-limiting example of a suitable aralkylthio group is benzylthio. The bond to the parent moiety is through the sulfur.

"Aralkoxy" means an aralkyl-O— group in which the aralkyl group is as described above. The bond to the parent moiety is through the oxygen group.

"Aralkoxycarbonyl" means an aralkyl-O—C(=O)— group. Non-limiting example of a suitable aralkoxycarbonyl group is benzyloxycarbonyl. The bond to the parent moiety is through the carbonyl.

"Aroyl" means an aryl-C(=O)— group in which the aryl group is as previously described. The bond to the parent moiety is through the carbonyl. Non-limiting examples of suitable groups include benzoyl and 1- and 2-naphthoyl.

"Aryl" (sometimes abbreviated "Ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Arylsulfonyl" means an aryl-S(O)$_2$— group. The bond to the parent moiety is through the sulfonyl.

"Arylsulfinyl" means an aryi-S(O)— group. The bond to the parent moiety is through the sulfinyl.

"Arylthio" means an aryl-S— group in which the aryl group is as previously described. Non-limiting examples of suitable arylthio groups include phenylthio and naphthylthio. The bond to the parent moiety is through the sulfur.

"Carboxyalkyl" means an alkyl-C(=O)O— group. The bond to the parent moiety is through the carboxy.

Carbamates and urea substituents refer to groups with oxygens and nitrogens respectively adjacent an amide; representative carbamate and urea substituents include the following:

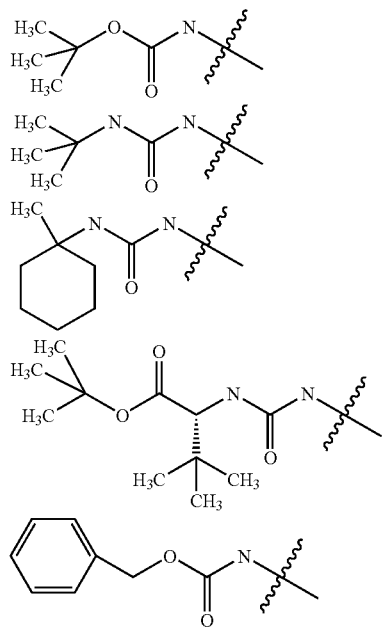

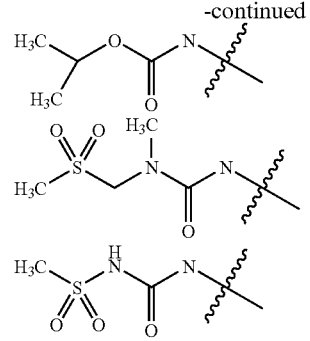

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Halogen" (or halo) means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above. Non-limiting examples include trifluoromethyl, 2,2,2-trifluoroethyl, 2-chloropropyl and alike.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. The nitrogen or sulfur atom of the heteroaryl can be optionally oxidized to the corresponding N-oxide, S-oxide or S,S-dioxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heterocyclenyl" means a partially unsaturated monocyclic or partially unsaturated multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heterocyclenyls contain about 5 to about 6 ring atoms and 1-3 double bonds. Preferred heterocyclenyls also contain at least one —C=N as part of the ring. The "heterocyclenyl" can be optionally substituted by one or more "ring system substituents" which may be the same or different, and are as defined herein. The prefix aza, oxa or thia before the heterocyclenyl root name means that at least a nitrogen, oxygen or sulfur atom respectively, is present as a ring atom. The nitrogen or sulfur atom of the heteroaryl can be optionally oxidized to the corresponding N-oxide, S-oxide or S,S-dioxide. Non-limiting examples of suitable heterocyclenyls include dihydroimidazole, dihydrooxazole, dihydrooxadiazole, dihydrothiazole, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, oxazolidinyl, imidazolidinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. Also included are ring systems comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Non-limiting examples of suitable monocyclic azaheterocyclic (i.e., azaheterocyclyl) groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, dihydro-2-pyrrolinyl, dihydro-3-pyrrolinyl, dihydro-2-imidazolinyl, dihydro-2-pyrazolinyl, dihydro-4,5-trizolyl and the like. Non-limiting examples of suitable oxaheterocyclic (i.e., oxaheterocyclyl) groups include 3,4-dihydro-2H-pyran, dihydrofuranyl, fluorodihydrofuranyl, and the like. Non-limiting example of a suitable multicyclic oxaheterocyclic group is 7-oxabicyclo[2.2.1]heptenyl. Non-limiting examples of suitable monocyclic thiaheterocyclic (i.e., thiaheterocyclyl) rings include dihydrothiophenyl, dihydrothiopyranyl, and the like.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-(3-yl)methyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl. The bond to the parent moiety is through the alkyl.

"Hydroxamate" means an alkyl-C(=O)NH—O— group. The bond to the parent moiety is through the oxygen group.

"Ring system substituent" means a substituent attached to an aromatic or non-aromatic ring system which, for example, replaces an available hydrogen on the ring system. Ring system substituents may be the same or different, each being independently selected from the group consisting of H, alkyl, alkenyl, alkynyl, alkoxyl, aryl, aroyl, aryloxy, cycloalkyl, cycloalkenyl, heteroaryl, heterocyclyl, alkylaryl, alkylheteroaryl, aralkyl, aralkenyl, aralkoxy, aralkoxycarbonyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), cyano, alkoxycarbonyl, hydroxyalkyl, carbonyl (non-limiting example(s) include ketone), —C(=O)heterocyclyl, formyl (non-limiting example(s) include aldehyde), carboxamido (i.e amido, —C(=O)NH$_2$), —C(=O)N(alkyl)$_2$, —C(=O)NH(alkyl), —C(=O)N(cycloalkyl)$_2$, —C(=O)NH(cycloalkyl), alkylC(=O)NH—, -amidino, hydrazido, hydroxamate, —NHC(=O)H, —NHC(=O)alkyl, urea (e.g —NH(C=O)NH$_2$), —NH(C=O)NH(alkyl), —NH(C=O)NH(alkyl)$_2$, —NH(C=O)NH(heteroaryl), —NH(C=O)NH(heterocyclyl), guanidinyl, —NHC(=NCN)NH$_2$, —NHC(=NCN)N(alkyl)$_2$, carbamoyl (i.e —CO$_2$NH$_2$), —NHC(=O)Oalkyl, —CO$_2$N(alkyl)$_2$, —NHC(=O)NH—S(O)$_2$alkyl, —NHC(=O)N(alkyl)$_2$—S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$,thio, alkylthiocarboxy, —S(O)$_2$alkyl, —S(O)$_2$aryl—OS(O)$_2$alkyl, —OS(O)$_2$aryl, sulfonyl urea (non-limiting example(s) include —NHC(=S)NHalkyl) and OSi(alkyl)$_3$.

"Spiroalkyl" means an alkylene group wherein two carbon atoms of an alkyl group are attached to one carbon atom of a parent molecular group thereby forming a carbocyclic or heterocyclic ring of three to eleven atoms. Representative structures include examples such as:

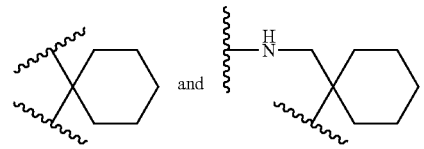

The spiroalkyl groups of this invention can be optionally substituted by one or more ring system substituents, wherein "ring system substituent" is as defined herein.

"Ring system substituent" also means a cyclic ring of 3 to 7 ring atoms of which may contain 1 or 2 heteroatoms, attached to an aryl, heteroaryl, or heterocyclyl ring by simultaneously substituting two ring hydrogen atoms on said aryl, heteroaryl, heterocyclyl ring. Non-limiting examples include:

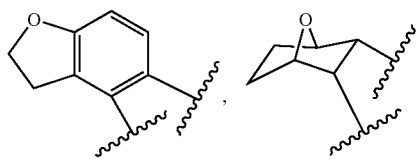

the like.

The term "optionally substituted" means optional substitution with the specified groups, radicals or moieties, in available position or positions.

With reference to the number of moieties (non-limiting example(s) include, substituents, groups or rings) in a compound, unless otherwise defined, the phrases "one or more" and "at least one" mean that, there can be as many moieties as chemically permitted, and the determination of the maximum number of such moieties is well within the knowledge of those skilled in the art. Preferably, there are one to three substituents, or more preferably, one to two substituents, with at least one in the para position.

As used herein, the term "composition" is intended to encompass a product comprising the specified ingredients in the specified amounts, as well as any product which results, directly or indirectly, from combination of the specified ingredients in the specified amounts.

The straight line ——as a bond generally indicates a mixture of, or either of, the possible isomers, non-limiting example(s) include, containing (R)— and (S)— stereochemistry. For example,

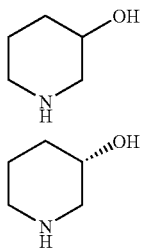

A dashed line (-----) represents an optional bond.

Lines drawn into the ring systems, such as, for example:

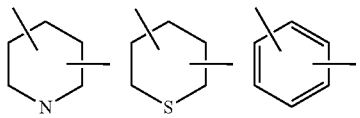

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

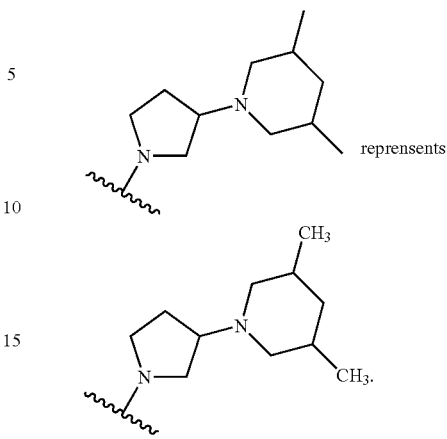

It should also be noted that any heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Metabolic conjugates", for example, glucuronides and sulfates which can undergo reversible conversion to compounds of Formula 1 are contemplated in this application.

"Effective amount" or "therapeutically effective amount" is meant to describe an amount of compound or a composition of the present invention effective to antagonize CXCR3 and thus produce the desired therapeutic effect in a suitable patient.

"Mammal" means humans and other mammalian animals.

"Patient" includes both human and animals.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$. In general, the solvated forms are equivalent to the unsolvated forms and are intended to be encompassed within the scope of this invention.

The compounds of Formula 1 form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (non-limiting example(s) include, non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (non-limiting example(s) include methyl, ethyl, propyl, and butyl chlorides, bromides and iodides), dialkyl sulfates (non-limiting example(s) include dimethyl, diethyl, dibutyl, and diamyl sulfates), long chain halides (non-limiting example(s) include decyl, lauryl, myristyl and stearyl chlorides, bromides and iodides), aralkyl halides (non-limiting example(s) include benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_1$-$C_4$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula 1, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate, ester and prodrug of enantiomers, stereoisomers, rotamers, tautomers, racemates or prodrugs of the inventive compounds.

It should also be noted that throughout the specification and Claims appended hereto any formula, compound, moiety or chemical illustration with unsatisfied valences is assumed to have the hydrogen atom to satisfy the valences unless the context indicates a bond.

In one embodiment, the present invention discloses compounds of Formula 1, having CXCR3 antagonist activity, or a pharmaceutically acceptable derivative thereof, where the various definitions are given above.

In another embodiment, L is O (i.e., oxygen).

In another embodiment, G is $R^2R^1X$—$C(R^{14})(R^{15})$—.

In another embodiment, wherein G is $R^2R^1X$—$C(R^{14})(R^{15})$—, X is N, and and $R^{14}$ and $R^{15}$ taken together is =O.

In another embodiment, wherein G is $R^2R^1X$—$C(R^{14})(R^{15})$—, X is N, and $R^{14}$ and $R^{15}$ taken together is =O, $R^1$ and $R^2$ are both H; i.e., $R^2R^1X$—$C(R^{14})(R^{15})$— is $H_2N$—(C=O)—.

In another embodiment, G is selected from the group consisting of H, hydroxyl, alkylO—, or $R^2R^1N$.

In another embodiment, the G 5-membered heteroaryl or heterocyclenyl ring containing at least one —C=N— moiety as part of said heteroaryl or heterocyclenyl ring, is selected from the group consisting of dihydroimidazole, imidazole, dihydrooxazole, oxazole, dihydrooxadiazole, oxadiazole, triazole, and tetrazole.

In another embodiment, G is selected from the group consisting of:

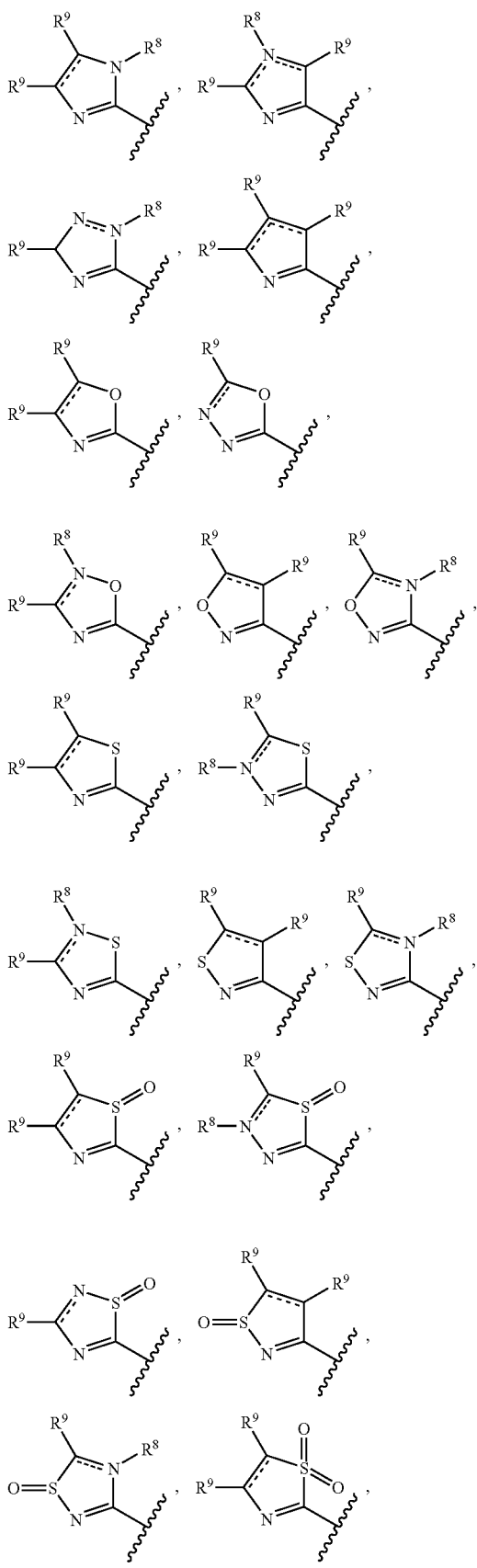

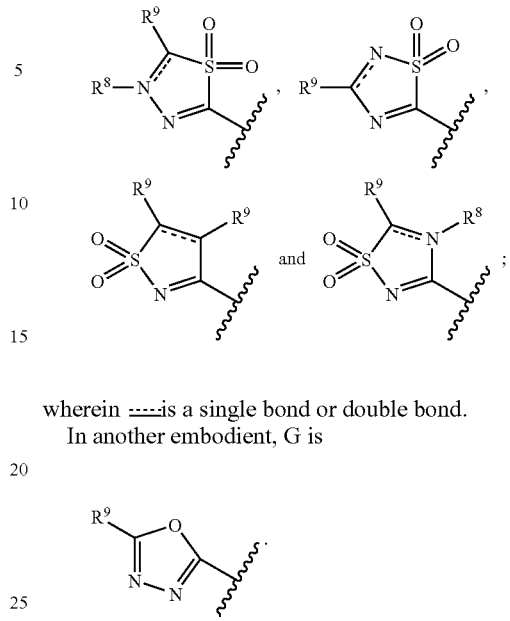

wherein ---- is a single bond or double bond.

In another embodient, G is

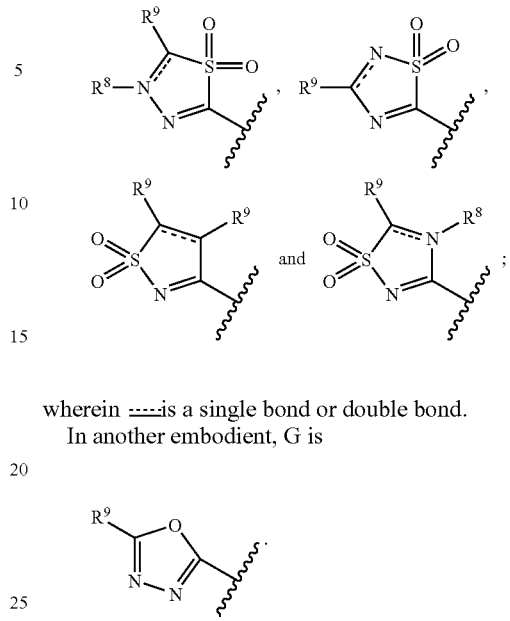

In another embodiment, $R^3$ is selected from the group consisting of H, alkyl, haloalkyl, hydroxyalkyl, halogen, —$N(R^{30})_2$, —$OR^{30}$ and —$CF_3$.

In another embodiment, $R^3$ is selected from the group consisting of H, —$CH_3$, —$CH_2CH_3$, cyclopropyl, —F, —Cl, $OCH_3$, $OCF_3$ and $CF_3$.

In another embodiment, $R^3$ is selected from the group consisting of H, —Cl and —$CH_3$.

In another embodiment, $R^8$ is selected from the group consisting of H, alkyl, alkenyl, arylalkyl, cycloalkyl, —$(CH_2)_q$OH, —$(CH_2)_qOR^{31}$, —$(CH_2)_qNH_2$, —$(CH_2)_q$ $NHR^{31}$, —$(CH_2)_qC(=)NHR^{31}$, —$(CH_2)_qSO_2R^{31}$, $(CH_2)_q$ $SO_2R^{31}$, and —$(CH_2)_qSO_2NHR^{31}$.

In another embodiment, $R^9$ moieties can be the same or different, each being independently selected from the group consisting of H, alkyl, cycloalkyl, —$C(=O)N(H)R^{30}$, —$C(=O)$alkyl, —$(CH_2)_q$OH, —$(CH_2)_qOR^{31}$, —$(CH_2)_q$ $NH_2$, —$(CH_2)_qNHR^{31}$, —$N(H)R^{30}$, —$N(H)S(O_2)R^{31}$, —$N(H)C(=O)NH(R^{30})$, —$OR^{30}$, —$SO_2(R^{31})$, and —$SO_2N$ $(H)R^{30}$.

In another embodiment, the $R^9$ moieties can be the same or different, each being independently selected from the group consisting of H, cyclopropyl, —$CF_3$, —$CH_3$, —$CH_2OH$, —$CH_2CH_2OH$, —$C(CH_3)_2OH$, —$CH_2CH_2OCH_3$, —$C(=O)OCH_2CH_3$, —$CH_2NH_2$, —$CH_2CH_2NH_2$, —$CH_2CH_2NHSO_2CH_3$, —$CH_2CH_2SO_2CH_3$, —$C(=O)$ $OCH_2CH_3$, —$C(=O)N(H)CH_2CH_2OH$, —$CH_2N(H)C$ $(=O)CF_3$, —$C(=O)N(H)$-cyclopropyl, —$C(=O)N(H)$ $CH_2CF_3$, —$NH_2$, —$NHCH_3$, —$N(CH_3)_2$, —$N(H)CH_2CH_3$, —$N(H)CH(CH_3)_2$, —$N(H)CH_2CH_2CH_3$, —$N(H)CH_2C$ $(=O)OCH_3$, —$N(H)CH_2CH_2OH$, —$N(H)CH_2CH_2NH_2$, —$N(H)CH_2CH_2NHSO_2CH_3$, —$N(H)CH_2CH_2SO_2CH_3$, —$N(H)C(=O)N(H)CH_2CH_3$, —$N(H)CH_2C(=O)NH_2$, —$OCH_3$, =S and =O.

In another embodiment, the $R^9$ moieties can be the same or different, each being independently selected from the group consisting of H, —$CF_3$, —$CH_3$, —$CH_2CH_2OH$, —$CH_2CH_2NH_2$, —$NH_2$, —$NHCH_3$, —$N(H)CH_2CH_3$, —$N(H)CH(CH_3)_2$, —$N(H)CH_2CH_2CH_3$, —$N(H)CH_2C$ $(=O)OCH_3$, and —$N(H)CH_2CH_2OH$.

In another embodiment, the $R^9$ moieties can be the same or different, each being independently selected from the group consisting of —$NH_2$ and —$N(H)CH_2CH_3$.

In another embodiment, $R^{10}$ is selected from the group consisting of H, alkyl, aralkyl, hydroxyalkyl, and carbonyl.

In another embodiment, $R^{10}$ is selected from the group consisting of —$CH_3$, —$CH_2CH_3$ and —$CH_2CH_2CH_3$, and m is 0-2.

In another embodiment, $R^{10}$ is —$CH_2CH_3$ and m is 1.

In another embodiment, $R^{11}$ is selected from the group consisting of H, alkyl, hydroxyalkyl and carbonyl.

In another embodiment, $R^{11}$ is H or —$CH_3$.

In another embodiment, $R^{11}$ is H.

In another embodiment, $R^{12}$ is selected from the group consisting of H, CN, —$C(=O)N(R^{30})_2$ and alkyl.

In another embodiment, $R^{12}$ is selected from the group consisting of H, —$CH_3$, CN and —$CH_2CH_3$.

In another embodiment, $R^{12}$ is H.

In another embodiment, the ring atoms of ring D are independently C or N and substituted by 0-4 $R^{20}$ moieties.

In another embodiment, ring D is a 5 to 6 membered aryl, heteroaryl, heterocyclenyl, or heterocyclyl ring and substituted by 0-4 $R^{20}$ moieties.

In another embodiment, ring D is a 5 to 6 membered aryl, or heteroaryl ring and substituted by 0-4 $R^{20}$ moieties.

In another embodiment, said ring D aryl ring is phenyl and said ring D heteroaryl ring is pyrindinyl.

In another embodiment, the $R^{20}$ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, aralkoxy, aryl, aryloxy, cyano, cycloalkyl, cycloalkenyl, halogen, haloalkyl, heteroalkyl, heteroaryl, heterocyclyl, hydroxyalkyl, trifluromethyl, trifluoromethoxy, —$(CH_2)_qOR^{31}$, —$(CH_2)_qNHR^{31}$, —$(CH_2)_qC(=O)NHR^{31}$, —$(CH_2)_qSO_2R^{31}$, —$(CH_2)_qNSO_2R^{31}$, —$(CH_2)_qSO_2NHR^{31}$, -alkynylC$(R^{31})_2OR^{31}$, —$C(=O)R^{30}$, —$C(=O)N(R^{30})_2$, —$C(=O)OR^{30}$, —$N(R^{30})_2$, —$N(R^{30})C(=O)R^{31}$, —$NHC(=O)N(R^{30})_2$, —$N(R^{30})C(=O)OR^{31}$, —$N(R^{30})C(=NCN)N(R^{30})_2$, —$N(R^{30})C(=O)N(R^{30})_2$, —$N(R^{30})SO_2(R^{31})$, —$N(R^{30})SO_2N(R^{30})_2$, —$OR^{30}$, —$OC(=O)N(R^{30})_2$, —$SR^{30}$, —$SO_2N(R^{30})_2$, —$SO_2(R^{31})$, —$OSO_2(R^{31})$, —$OSi(R^{30})_3$.

In another embodiment, the $R^{20}$ moieties can be the same or different, each being independently selected from the group consisting of H, alkyl, amino, halogen, CN, $CH_3$, $CF_3$, $OCF_3$, —$(CH_2)_qOR^{31}$, —$(CH_2)_qNHR^{31}$, —$(CH_2)_qC(=O)NHR^{31}$, —$(CH_2)_qSO_2R^{31}$, —$(CH_2)_qNSO_2R^{31}$, —$(CH_2)_qSO_2NHR^{31}$, -alkynylC$(R^{31})_2OR^{31}$, —$C(=O)R^{30}$, —$C(=O)OR^{30}$, —$N(R^{30})_2$, —$N(R^{30})C(=O)R^{31}$, —$NHC(=O)N(R^{30})_2$, —$N(R^{30})C(=O)OR^{31}$, —$N(R^{30})C(=NCN)N(R^{30})_2$, —$N(R^{30})C(=O)N(R^{30})_2$, —$OR^{30}$, —$OC(=O)N(R^{30})_2$, and —$OSO_2(R^{31})$.

In another embodiment, the $R^{20}$ moieties can be the same or different, each being independently selected from the group consisting of H, halogen, and amino.

In another embodiment, Y is selected from the group consisting of: —$(CHR^{13})_r$—, —$(CR^{13}R^{13})_r$—, —$C(=O)$— and —$CHR^{13}C(=O)$—.

In another embodiment, Y is selected from the group consisting of: —$CH_2$—, —$CH(CH_3)$—, —$CH(CH_2OH)$—, —$C(=O)$— and —$CH(CO_2alkyl)$-.

In another embodiment, Y is selected from the group consisting of: —$CH_2$—, and —$C(=O)$—.

In another embodiment, m is 0-2.

In another embodiment, m is 1.

In another embodiment, n is 0-2.

In another embodiment, n is 0.

In another embodiment, q is 1 or 2.

In another embodiment, r is 1 or 2.

In another embodiment, G is selected independently from the group consisting of $R^2R^1N$—$C(=O)$— and

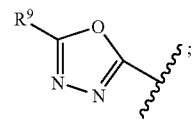

$R^3$ is selected from the group consisting of H, —Cl and —$CH_3$;

$R^9$ is selected from the group consisting of —$NH_2$ and —$N(H)CH_2CH_3$;

$R^{10}$ is —$CH_2CH_3$;

$R^{11}$ is H;

$R^{12}$ is H;

ring D is a a 5 to 6 membered aryl, or heteroaryl ring and substituted by 0-4 $R^{20}$ moieties;

$R^{20}$ moieties can be the same or different, each being independently selected from the group consisting of H, halogen, and amino;

Y is selected from the group consisting of: —$CH_2$—, and —$C(=O)$—;

m is 1; and n is 0.

In another embodiment, the compound of Formula 1 is is selected from the group consisting of the following:

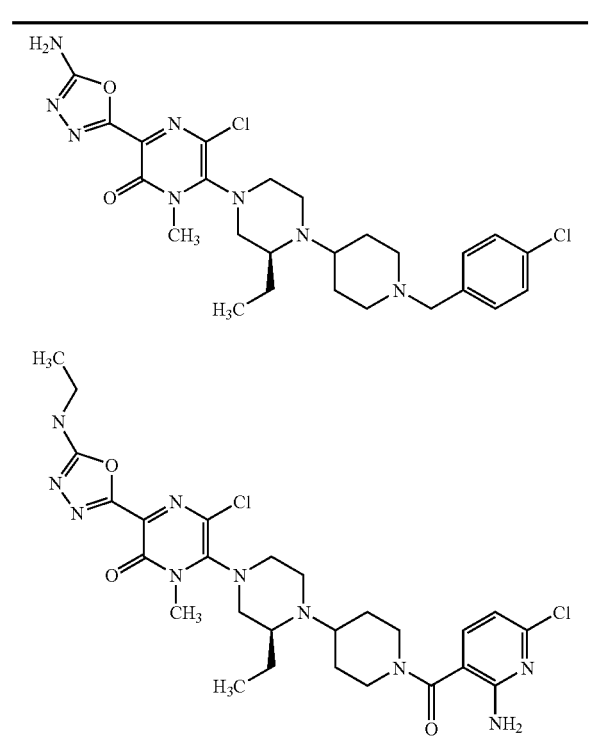

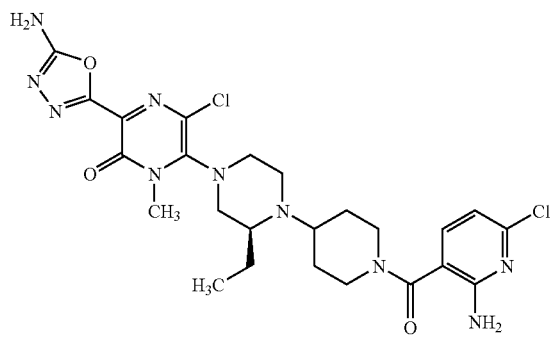
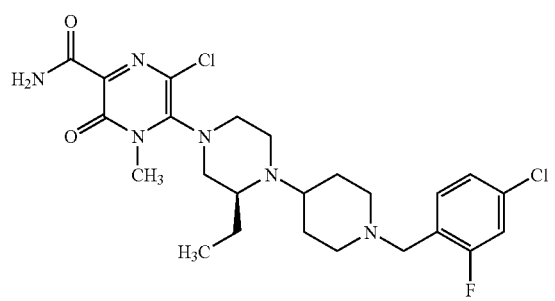
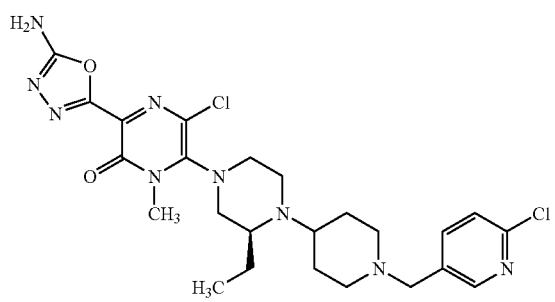
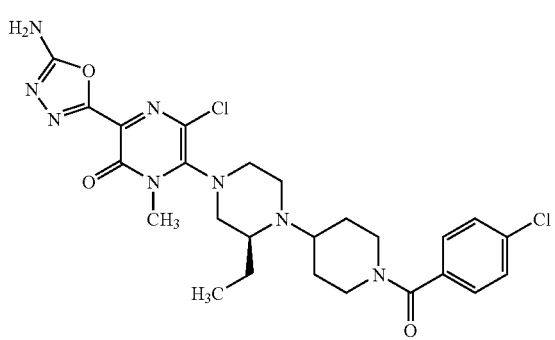
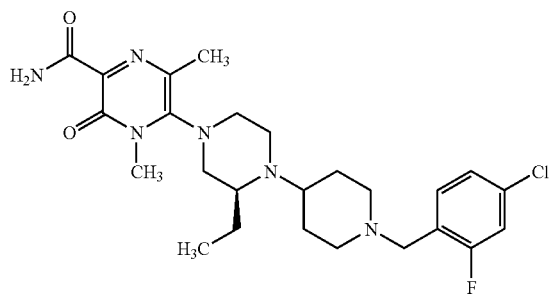
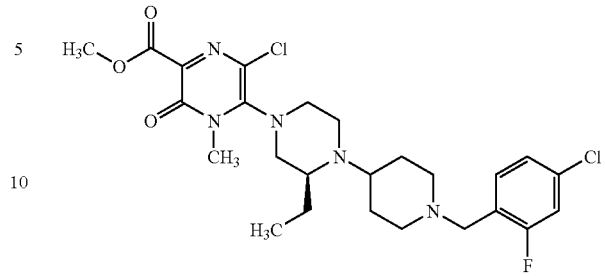
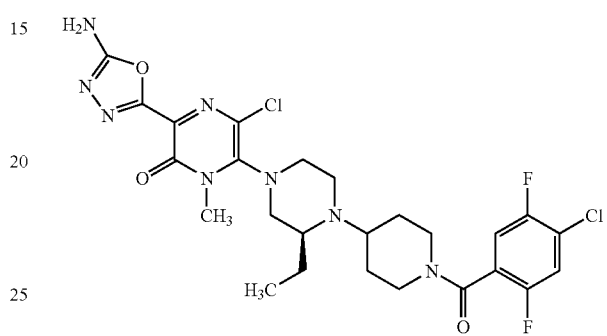
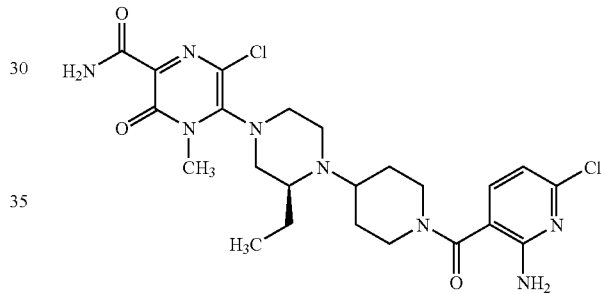
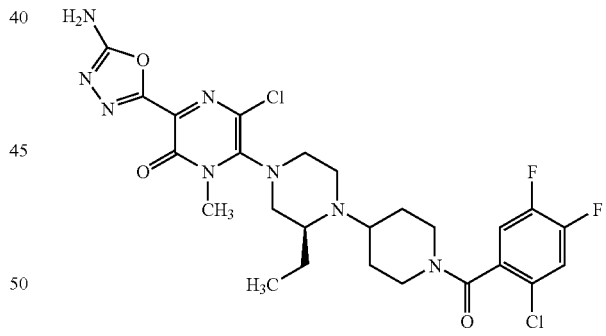
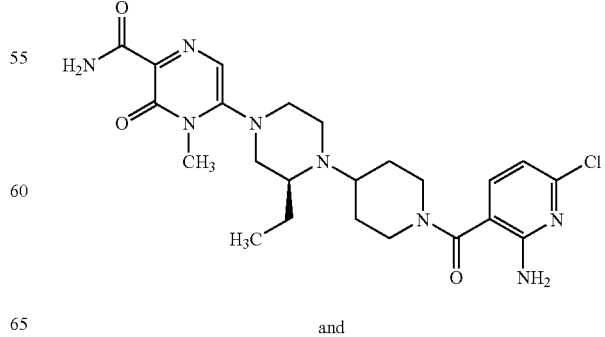
and

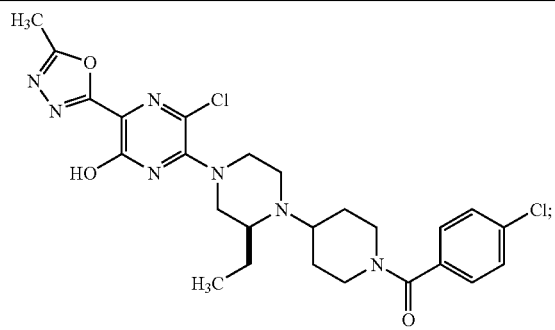

or a pharmaceutically acceptable salt, solvate or ester thereof.

In another embodiment, the compound is selected from the group consisting of

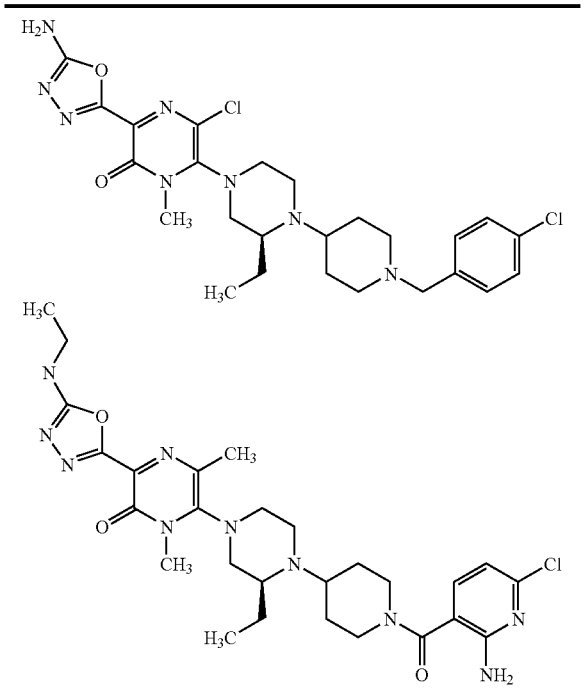

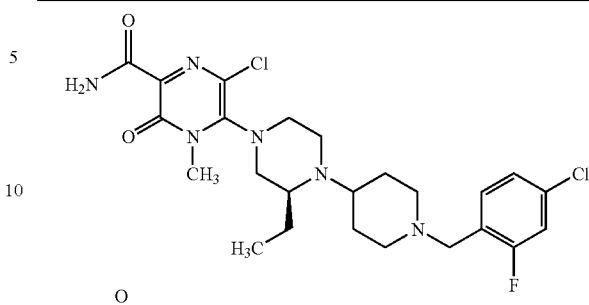

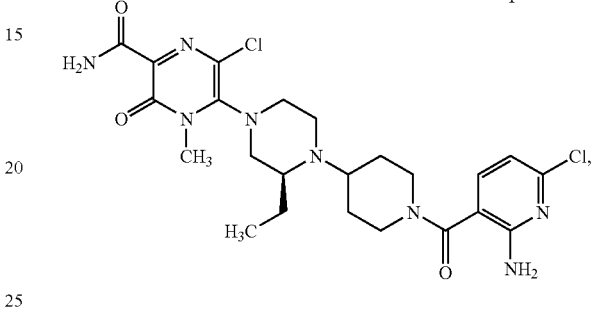

and

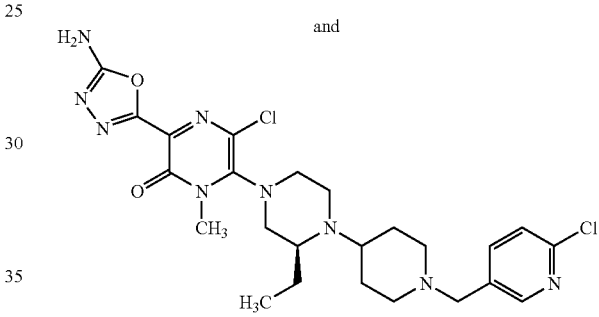

or a pharmaceutically acceptable salt, solvate or ester thereof.

In still another embodiment of the present invention, a compound is selected from the following structures in Table 1 below (or pharmaceutically acceptable salts, solvates or esters thereof) which are shown along with their Ki ratings. The Ki values are rated, "A" for Ki values less than about 25 nanomolar (nM), "B" for Ki values in the range of from about 25 to about 100 nM and "C" for Ki values greater than about 100 nM. For instance, Compound Number 1 has a Ki of 1.9 nM, and therefore has a rating of "A".

TABLE 1

| Compound Number | STRUCTURE | Ki rating |
|---|---|---|
| 1 | 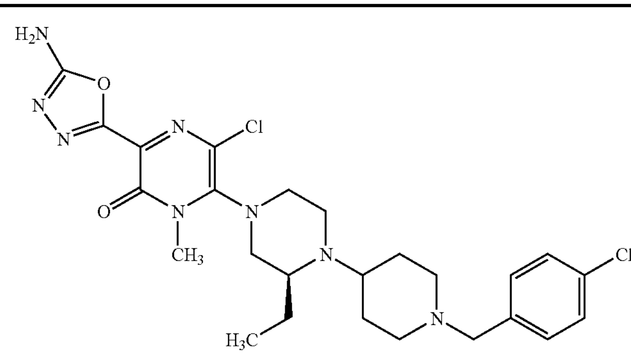 | A |

TABLE 1-continued

| Compound Number | STRUCTURE | Ki rating |
|---|---|---|
| 2 | 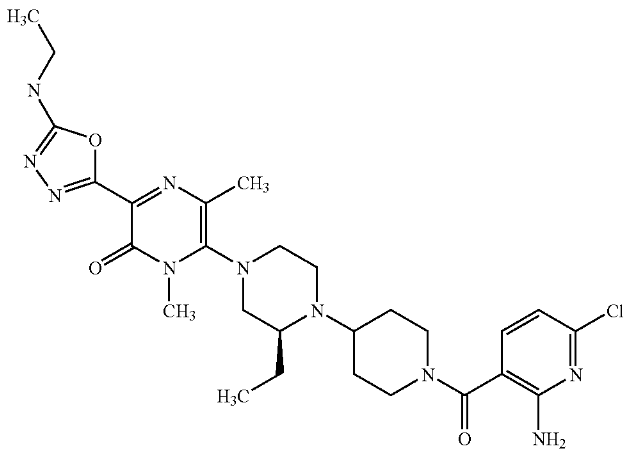 | A |
| 3 | 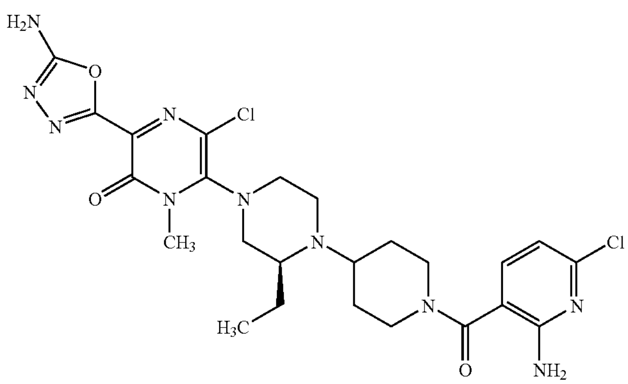 | A |
| 4 | 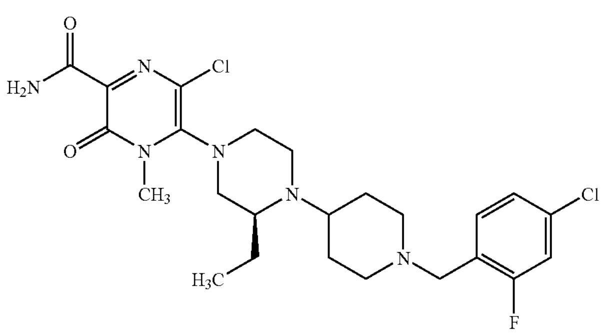 | A |
| 5 | 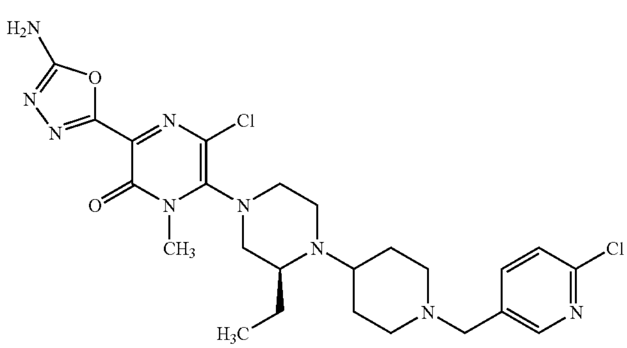 | A |

TABLE 1-continued

| Compound Number | STRUCTURE | Ki rating |
|---|---|---|
| 6 | 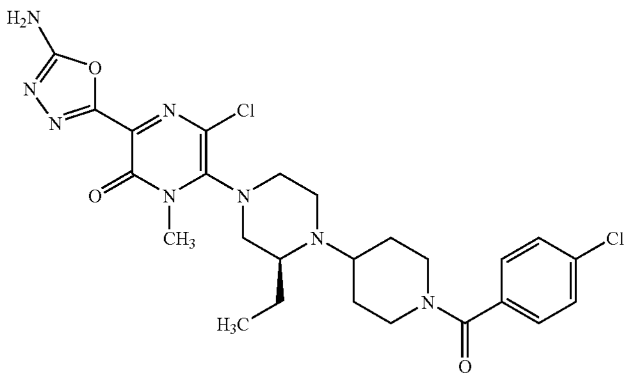 | B |
| 7 | 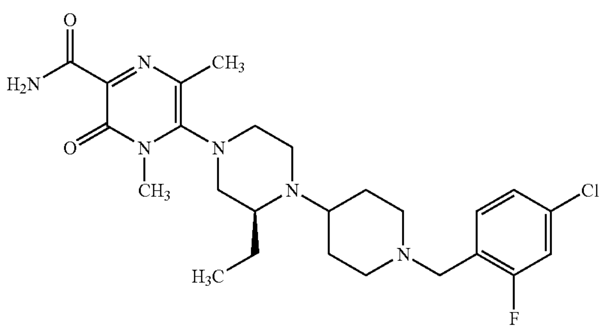 | B |
| 8 | 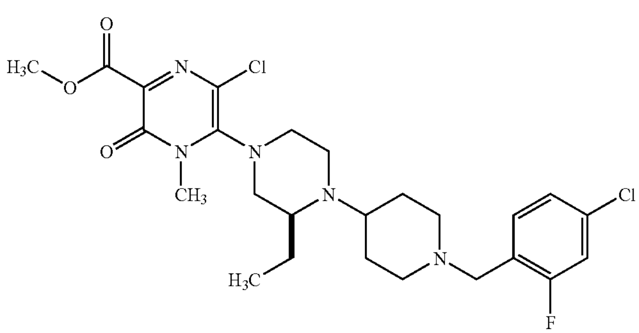 | B |
| 9 | 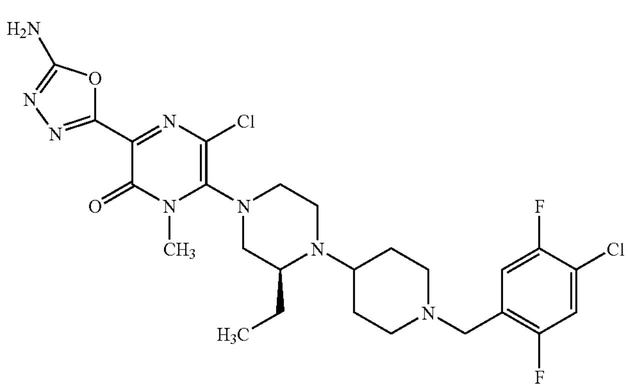 | B |

TABLE 1-continued

| Compound Number | STRUCTURE | Ki rating |
|---|---|---|
| 10 | [Structure: pyrazinone with carboxamide, Cl, N-methyl, ethyl-piperazine, piperidine-CH2-(2-amino-6-chloropyridin-3-yl)] | B |
| 11 | [Structure: 2-amino-1,3,4-oxadiazole-pyrazinone with Cl, N-methyl, ethyl-piperazine, piperidine-CH2-(2-chloro-4,5-difluorophenyl)] | B |
| 12 | [Structure: pyrazinone with carboxamide, N-methyl, ethyl-piperazine, piperidine-CH2-(2-amino-6-chloropyridin-3-yl)] | C |
| 13 | [Structure: 2-amino-1,3,4-oxadiazole-hydroxypyrazine with Cl, ethyl-piperazine, piperidine-CH2-(4-chlorophenyl)] | C |

Examples of represenative compounds with specific Ki values are set forth in Table 2 below:

| Compound Number | STRUCTURE | Ki |
|---|---|---|
| 1 | 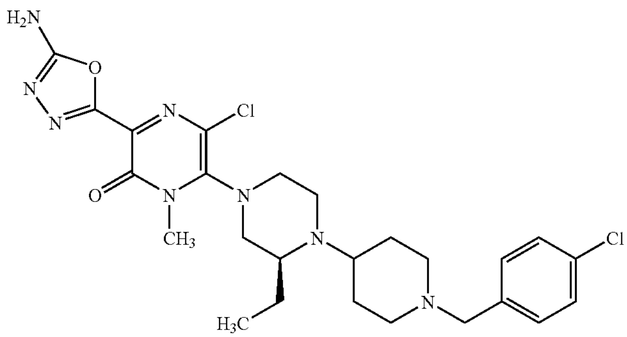 | 1.9 |
| 2 | 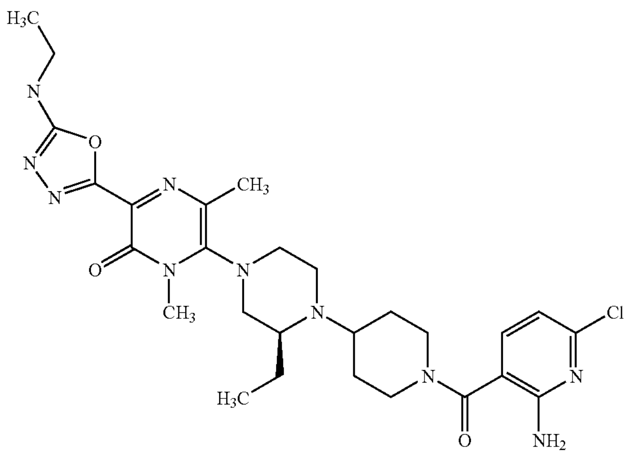 | 2.6 |
| 3 | 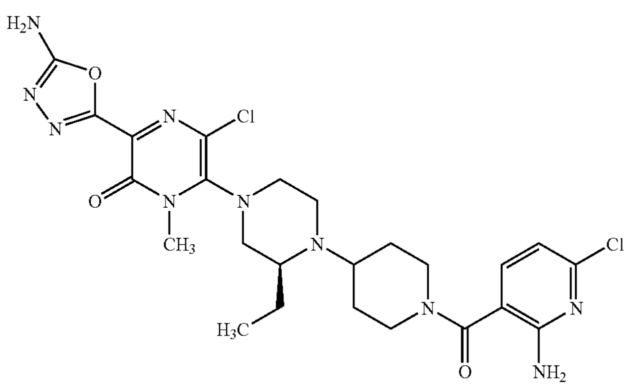 | 7.5 |
| 4 | 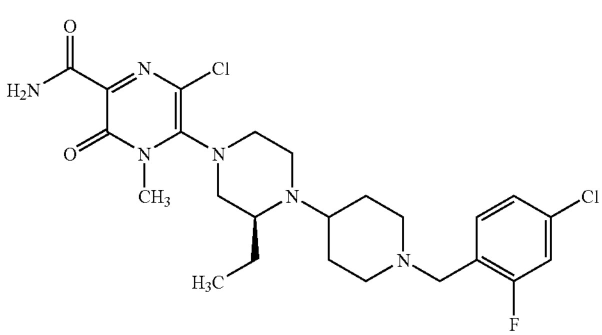 | 8.3 |

-continued

| Compound Number | STRUCTURE | Ki |
|---|---|---|
| 5 | [structure] | 1.9 |

In yet another aspect, the compound according to Formula 1 is in purified form.

In another embodiment, this invention provides a pharmaceutical composition comprising at least one compound of Formula 1, or a pharmaceutically acceptable salt, solvate or ester thereof in combination with at least one pharmaceutically acceptable carrier.

In still another embodiment, the invention provides a pharmaceutical composition of Formula 1, further comprising at least one additional agent, drug, medicament, antibody and/or inhibitor for treating a CXCR3 chemokine receptor mediated disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of Formula III and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In yet another embodiment, the present invention discloses methods for preparing pharmaceutical compositions comprising the inventive heterocyclic substituted piperazine compounds of Formula 1 as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution—refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrol idone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

It will be apparent to those skilled in the art that many modifications, variations and alterations to the present disclosure, both to materials and methods, may be practiced. Such modifications, variations and alterations are intended to be within the spirit and scope of the present invention.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention. Certain compounds of the present invention may exist in multiple crystalline forms or amorphous forms. All physical forms of the current invention are contemplated.

Compounds of this invention which contain unnatural proportions of atomic isotopes (i.e. "radiolabeled compounds") whether their use is therapeutic, diagnostic or as a research reagent are contemplated under this invention.

Another embodiment of the invention discloses the use of the pharmaceutical compositions disclosed above for treatment of diseases of a CXCR3 chemokine receptor mediated disease in a patient in need of such treatment comprising administering to the patient a therapeutically effective amount of at least one compound according to Formula 1, or a pharmaceutically acceptable salt, solvate or ester thereof.

In another embodiment, the method is directed to administering to the patient (a) an effective amount of at least one compound according to Formula 1, or a pharmaceutically acceptable salt, solvate or ester thereof concurrently or sequentially with (b) at least one additional agent, drug, medicament, antibody and/or inhibitor for treating a CXCR3 chemokine receptor mediated disease, in combination with a pharmaceutically acceptable carrier.

In another embodiment, at least one compound of Formula 1 binds to a CXCR3 receptor.

The method can further comprise administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (Non-limiting examples include methotrexate, cyclosporin, FK506); steroids; PDE IV inhibitors, anti-TNF-$\alpha$ compounds, TNF-alpha-convertase inhibitors, cytokine inhibitors, MMP inhibitors, glucocorticoids, chemokine inhibitors, CB2-selective inhibitors, p38 inhibitors, biological response modifiers; anti-inflammatory agents and therapeutics. The disease can be an inflammatory disease.

Another embodiment of this invention is directed to a method of inhibiting or blocking T-cell mediated chemotaxis in a patient in need of such treatment the method comprising administering to the patient a therapeutically effective amount of at least one compound according to Formula 1 or a pharmaceutically acceptable salt, solvate or ester thereof.

Another embodiment of this invention is directed to a method of treating inflammatory bowel disease in a patient in need of such treatment comprising administering to the patient a therapeutically effective amount of at least one compound according to Formula 1, or a pharmaceutically acceptable salt, solvate or ester thereof.

Another embodiment of this invention is directed to a method of treating or preventing graft rejection in a patient in need of such treatment comprising administering to the patient a therapeutically effective amount of at least one compound according to Formula 1, or a pharmaceutically acceptable salt, solvate or ester thereof.

Another embodiment of this invention is directed to a method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: cyclosporine A, FK-506, FTY720, beta-Interferon, rapamycin, mycophenolate, prednisolone, azathioprine, cyclophosphamide and an antilymphocyte globulin.

Another embodiment of this invention is directed to a method of treating multiple sclerosis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: beta-interferon, glatiramer acetate, glucocorticoids, methotrexate, azothioprine, mitoxantrone, VLA-4 inhibitors and/or CB2-selective inhibitors.

Another embodiment of this invention is directed to a method of treating multiple sclerosis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: methotrexate, cyclosporin, leflunimide, sulfasalazine, $\beta$-methasone, $\beta$-interferon, glatiramer acetate, prednisone, etonercept, and. infliximab.

Another embodiment of this invention is directed to a method of treating rheumatoid arthritis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: COX-2 inhibitors, COX inhibitors, immunosuppressives, steroids, PDE IV inhibitors, anti-TNF-$\alpha$ compounds, MMP inhibitors, glucocorticoids, chemokine inhibitors, CB2-selective inhibitors, caspase (ICE) inhibitors and other classes of compounds indicated for the treatment of rheumatoid arthritis.

Another embodiment of this invention is directed to a method of treating psoriasis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, steroids, and anti-TNF-$\alpha$ compounds.

Another embodiment of this invention is directed to a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, tuberculoid leprosy, type I diabetes, viral meningitis and tumors in a patient in need of such treatment, such method comprising administering to the patient an effective amount of at least one compound according to Formula 1, or a pharmaceutically acceptable salt, solvate or ester thereof.

Another embodiment of this invention is directed to a method of treating a disease selected from the group consisting of inflammatory disease, rheumatoid arthritis, multiple sclerosis, inflammatory bowel disease, graft rejection, psoriasis, fixed drug eruptions, cutaneous delayed-type hypersensitivity responses, tuberculoid leprosy and cancer in a patient in need of such treatment, such method comprising administering to the patient an effective amount of at least one compound according to Formula 1, or a pharmaceutically acceptable salt, solvate or ester thereof.

Another embodiment of this invention is directed to a method of treating a disease selected from the group consisting of inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives; steroids; PDE IV inhibitors, anti-TNF-α compounds, MMP inhibitors, glucocorticoids, chemokine inhibitors, CB2-selective inhibitors, biological response modifiers; anti-inflammatory agents and therapeutics.

Another embodiment of the invention discloses a method of making the substituted pyrazine compounds, disclosed above.

Unless otherwise stated, the following abbreviations have the stated meanings in the Examples below:
DBU=1,8-diazabicyclo[5.4.0]undec-7-ene
DBN=1,5-diazabicyclo[4.3.0]non-5-ene
DMF=N,N-dimethylformamide
Et$_2$O=diethyl ether
EDCl=1-(3-dimethylaminopropyl)-3-ethylcarbodiimide
HOBT=1-hydroxybenzotriazole
DCC=dicyclohexylcarbodiimide
Dibal-H=diisobutylaluminum hydride
LAH=lithium aluminum hydride
NaBH(OAc)$_3$=sodium triacetoxyborohydride
NaBH$_4$=sodium borohydride
NaBH$_3$CN=sodium cyanoborohydride
LDA=lithium diisopropylamide
p-TsOH=p-toluenesulfonic acid
m-CPBA=m-Chloroperbenzoic acid
TMAD=N,N,N',N'-tetramethylazodicarboxamide
CSA=camphorsulfonic acid
NaHMDS=sodium hexamethyl disilylazide
THF=tetrahydrofuran
HRMS=High Resolution Mass Spectrometry
HPLC=High Performance Liquid Chromatography
LRMS=Low Resolution Mass Spectrometry
nM=nanomolar
Ki=Dissociation Constant for substrate/receptor complex
pA2=-log EC$_{50}$, as defined by J. Hey, *Eur. J. Pharmacol.*, (1995), Vol. 294, 329-335.
Ci/mmol=Curie/mmol (a measure of specific activity)
Tr=Triphenylmethyl
TRIS=Tris (hydroxymethyl)aminomethane General Synthesis Compounds of the present invention can be prepared by a number of ways evident to one skilled in the art. Preferred methods include, but are not limited to, the general synthetic procedures described herein. One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (i.e. non-linear or preassembly of certain portions of the molecule) is a more efficient method of assembly of the target compounds. Mehthods for the preparation of compounds of general formula 1 where variables (R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{30}$, R$^{31}$, G, L, Z, X, D, Y, m, n, p and q) are as defined above, are shown in scheme 1, 2, and 3. Pr$^1$, Pr$^2$ and Pr$^3$ are protecting groups exemplified below.

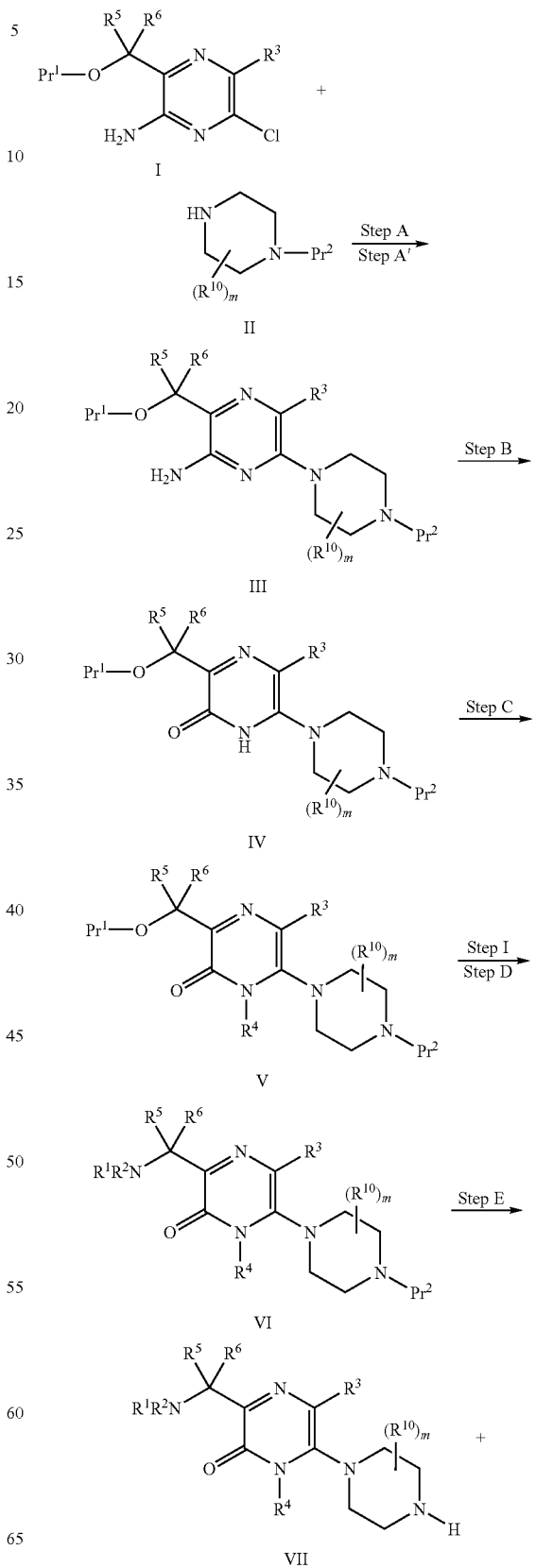

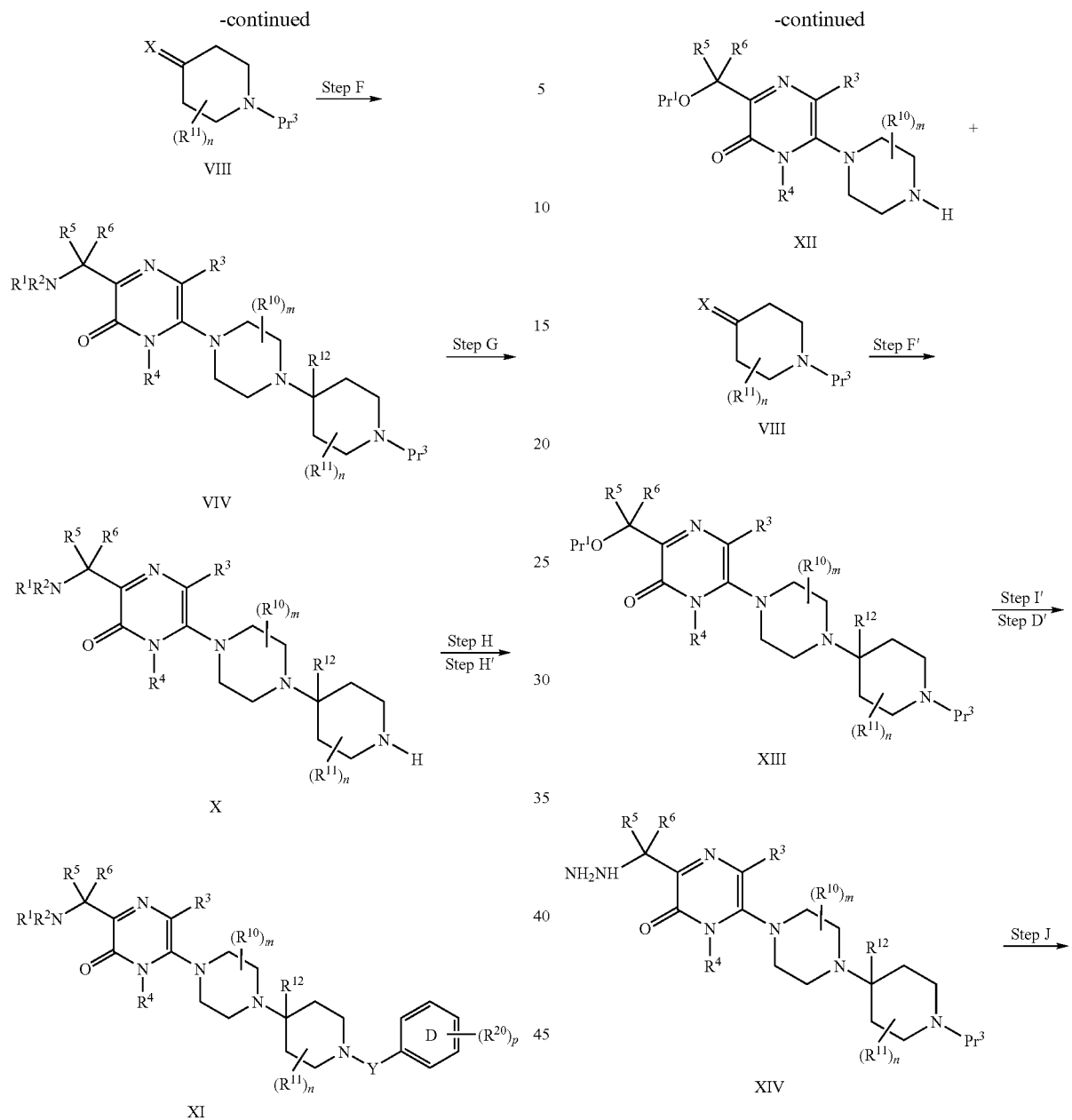
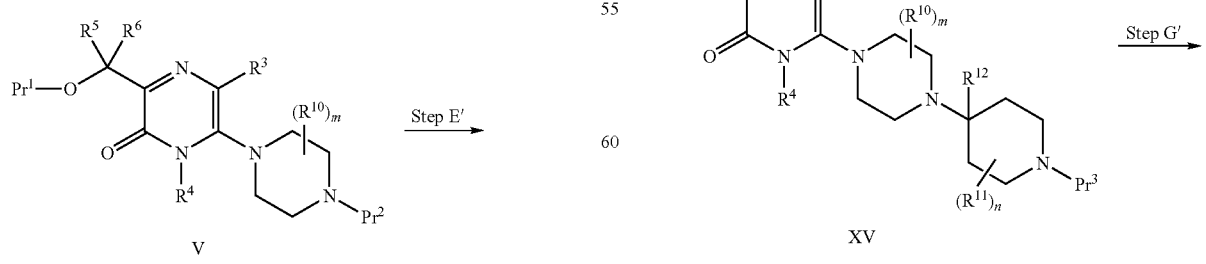

-continued
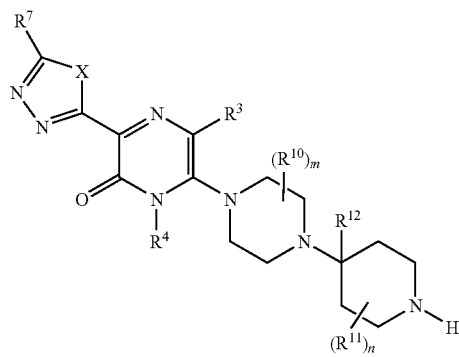
XV
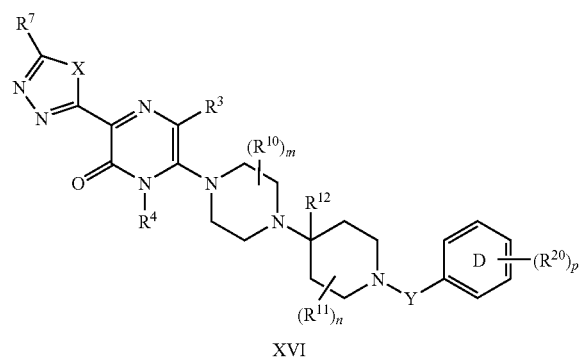
XVI
Scheme 3. Method C.
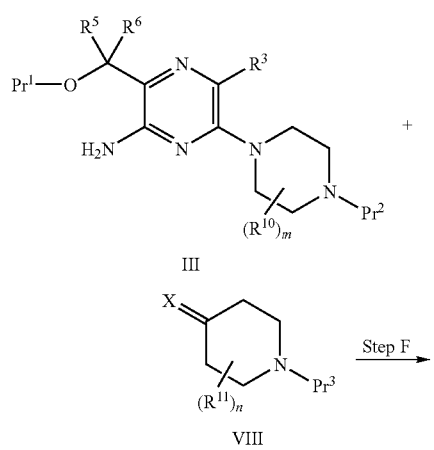
III
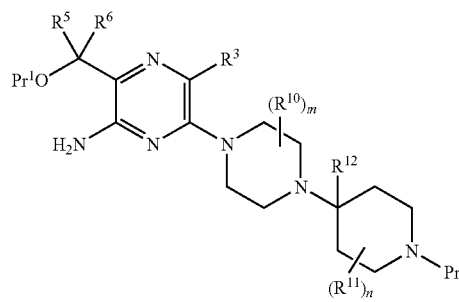
XVII
-continued
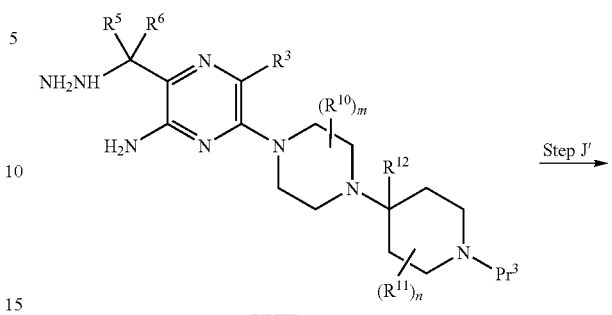
XVIII
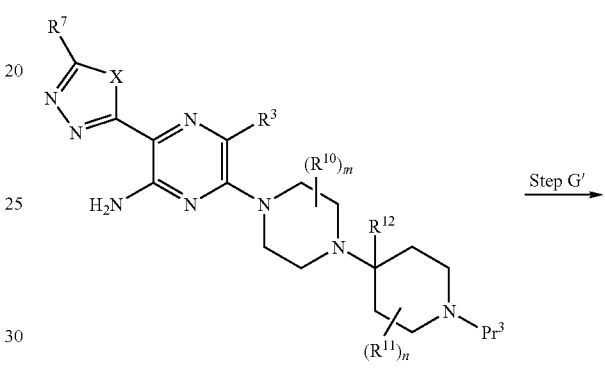
XIX
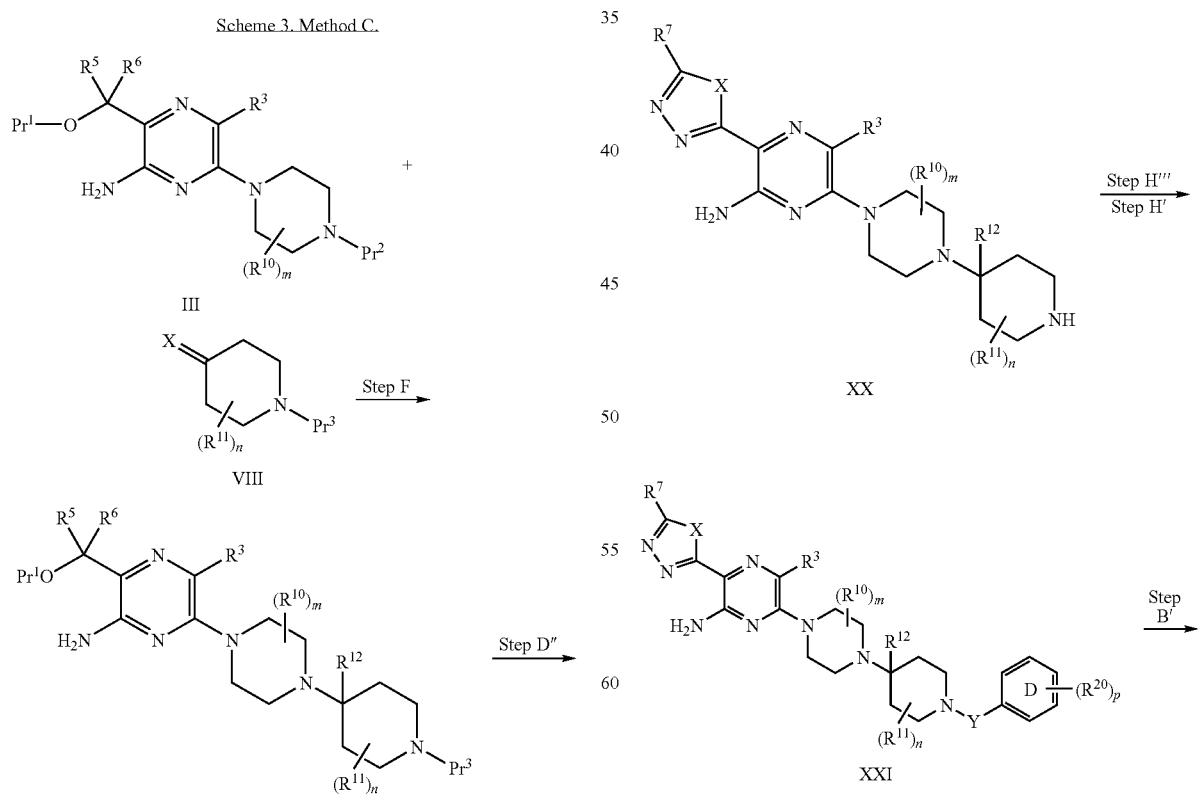
XX
XXI -continued

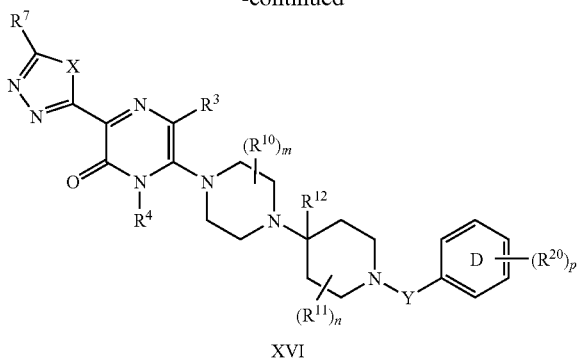

XVI

The staring material and reagents used in preparing compounds described are either available from commercial suppliers such as Aldrich Chemical Co. Wisconsin, USA) and Acros Organics Co. (New Jersey, USA) or were prepared y literature methods known to those skilled in the art.

The preparation of arylpiperazine compounds related to intermediate III has been reported in WO-03037862 (Nippon Shinyaku).

One skilled in the art will recognize that the synthesis of compounds of formula 1 may require the need for the protection of certain functional groups (i.e. derivatization for the purpsose of chemical compatibility with a particular reaction condition). A suitable protecting group for an carboxyilc acid (Pr$^1$, when R$^{14}$, R$^{15}$=O) is the methyl, ethyl , isopropyl, or benzyl ester and alike. A suitable protecting group for an amine (Pr$^2$, Pr$^3$) is methyl, benzyl, ethoxycarbonyl, t-butoxycarbonyl, benzyloxy carbonyl, phthaloyl, trifluoroacetyl, acetyl and alike. All protecting groups can be appended to and removed by literature methods known to those skilled in the art.

One skilled in the art will recognize that the synthesis of compounds of formula 1 may require the construction of an amide bond. Methods include but are not limited to the use of a reactive carboxyl derivative (e.g. acid halide, or ester at elevated temperatures) or the use of an acid with coupling reagents (e.g. EDCl, DCC) in the presence of an amine at 0° C. to 100° C. Suitable solvents for the reaction are halogenated hydrocarbons, ethereal solvents, DMF and alike. The reaction may be conducted under pressure or in a sealed vessel.

One skilled in the art will recognize that the synthesis of compounds of formula 1 may require the construction of an amine bond. One such method is but not limited to the reaction of a primary or secondary amine with a reactive carbonyl (e.g. aldehyde or ketone) under reductive amination conditions. Suitable reducing agents of the intermediate imine are NaBH$_4$, NaBH(OAc)$_3$ and alike at 0° C. to 100° C. Suitable solvents for the reaction are halogenated hydrocarbons, ethereal solvents, DMF and alike. Optionally, the reaction can be performed in the presence of titanium tetraisopropoxide to facilitate the imine generation. Another such method is but not limited to the reaction of a primary or secondary amine with a reactive alkylating agent such as an alkyl halide, benzyl halide, mesylate, tosylate and alike. Suitable solvents for the reaction are halogenated hydrocarbons, ethereal solvents, DMF and alike. The reaction may be conducted under pressure or in a sealed vessel at 0° C. to 100° C.

One skilled in the art will recognize that the synthesis of compounds of formula 1 may require the reduction of a reducible functional group. Suitable reducing agents include NaBH$_4$, LAH, diborane and alike at −20° C. to 100° C. Suitable solvents for the reaction are halogenated hydrocarbons, ethereal solvents, DMF and alike.

One skilled in the art will recognize that the synthesis of compounds of formula 1 may require the oxidation of a functional group. Suitable oxidizing reagents include oxygen, hydrogen peroxide, m-CPBA and alike at −20° C. to 100° C. Suitable solvents for the reaction are halogenated hydrocarbons, ethereal solvents, water and alike.

The starting materials and the intermediates of a reaction may be isolated and purified if desired using conventional techniques, including but not limited to filtration, distillation, crystallization, chromatography and alike. Such materials can be characterized using conventional means, including physical constants and spectral data.

General Description of Methods

Step A. Amination of 2-Halopyrazine

A suitably protected 2-halopyrazine of formula I is reacted with a piperazine of formula II to form a compound of general formula III. Preferably the reaction is carried out in a solvent such as dioxane in the presence of a base such as potassium carbonate or cesium carbonate.

Step A'. Protection on Piperazine amine

Optionally, if the 2-halopyrazine of formula I is reacted with unprotected piperazine II (where Pr2=H), the product of formula III needs to be protected with a suitable amine protecting group described above.

Step B. Sandmyer Type Reaction

A suitably protected 2-halopyrazine of formula III is reacted with an alkyl nitrite in the presence of acid to form a compound of general formula IV. Preferably the reaction is carried out in a solvent such as THF and water.

Alternatively, a fully assembled 6-aminopyrazine of formula XXI is reacted under the same reaction condition described above to provide a compound of general formula XVI Step C. N-Alkylation of 2-Pyrazinone A suitably protected 2-pyrazinone of formula IV is reacted with a alkylating agent such as methyl iodide to form a N-alkylated product of general formula V. Preferably the reaction is carried out in a solvent such as acetone in the presence of a base such as potassium carbonate or cesium carbonate.

Step D. Amidation of an Ester

A suitably protected alkyl ester of formula V (when R$^{14}$, R$^{15}$=O) is reacted with an amine to afford an amide of general formula VI. Preferably the reaction is carried out in a solvent such as methanol or dioxane in a pressure vessel at 25° C. to 100° C.

Step D'. Hydrazide Formation

A suitably protected alkyl ester of formula XIII (when R$^{14}$, R$^{15}$=O) is reacted with a hydrazide (substituted or non-substituted) to afford a hydrazide of general formula XIV. Preferably the reaction is carried out in a polar solvent such as MeOH or EtOH at 25° C. to 100° C.

Step E. Deprotection of Amine Protecting Group

Optionally, if the product of step A is a protected piperazine of structure III, deprotection is required. When Pr2 is benzyl or substituted benzyl, deprotection can be effected by reaction under a pressure of hydrogen gas in the presence of a catalyst such as palladium. When Pr2 is ethoxycarbonyl deprotection can be effected by reaction with trimethylsilyl iodide. When Pr2 is t-butoxycarbonyl deprotection can be effected with a strong acid such as trifluoroacetic acid.

Step F. Reductive Amination

A piperazine of structure VII is reacted with a ketone of structure VIII in the presence of a reducing agent with or without titanium tetraisopropoxide to form a compound of structure VIV where R12 is hydrogen. General conditions for the reductive amination reaction are described above.

Step G. Deprotection of Amine Protecting Group

Optionally, if the ketone of step F is a protected piperazine of structure VIII, deprotection is required. When Pr3 is benzyl or substituted benzyl deprotection can be effected by reaction under a pressure of hydrogen gas in the presence of a catalyst such as palladium. When Pr3 is ethoxycarbonyl deprotection can be effected by reaction with trimethylsilyl iodide. When Pr3 is t-butoxycarbonyl deprotection can be effected with a strong acid such as trifluoroacetic acid.

Step H. Amide formation when Y=C=O

A compound of structure X is reacted with a reactive carboxyl derivatives (acid halide or ester) or the corresponding acids in general conditions described above.

Step H. Amine formation when Y=CR1R2

A compound of structure X is reacted with a reactive carbonyl derivatives (aldehyde or ketone) under the reductive amination condition described above. Another methods include using alkylating agents such as alkyl halide, benzyl halide, mesylate, tosylate or alike. General conditions are described above.

Step H'.

Optionally, functional group manipulation of a compound of structure XI or XVI may be done to provide additional related compounds of structure XI or XVI.

Step I. Suzuki Coupling

A suitably protected ester of formula XIII where $R^{14}=R^{15}=O$ and R3=Cl is reacted with an alkylboronic aicd in the presence of an appropriate palladium catalyst and ligands under the typical Suzuki coupling condition. Preferably, the reaction is carried out in a solvent such as DMF or THF in the presence of a bsae such as potassium carbonate or nodium carbonate at 25° C. to 100° C.

Step J. Formation of Heterocycle Moiety

A suitably protected hydrazide of formula XIV where $R^{14}=R^{15}=O$ and Pr3 is a amine protecting group described above, is reacted with an acylating reagent to provide a heterocycle in the presence of a dehydrating agent such as p-toluenesulfonyl chloride. Typically the reaction is carried out in a solvent such as THF or acetonitrile at 25° C. to 100° C.

Compounds of formula 1, can be prepared by the general methods outlined in schemes 1, 2, and 3. Synthesis of the specifically exemplified compounds were prepared as described in detailed below. The following EXAMPLES are being provided to further illustrate the present invention. They are for illustrative purposes only; the scope of the invention is not to be considered limited in any way thereby.

EXAMPLES

Example 1

Step A, Method A

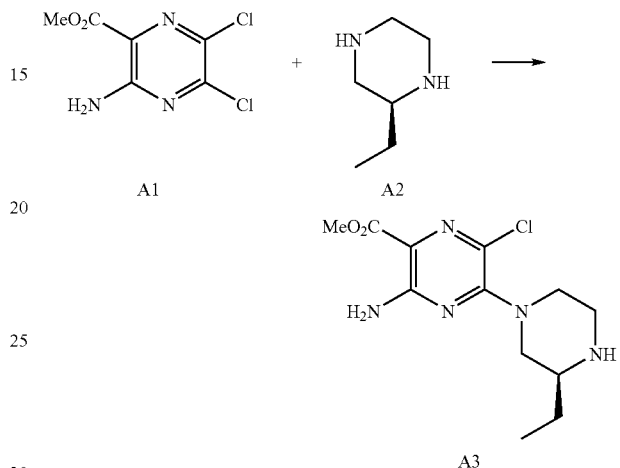

A round bottomed flask was charged with methyl 6-amino 2,3-dichloro pyrazine 5-carboxylate (Aldrich, 25 g, 112.6 mmol), 2-S-ethyl piperazine (prepared as per Williams et al J. Med. Chem 1996, 39, 1345, 83% active, 15.7 g, 112.7 mmol), cesium carbonate (100 g, 300 mmol) and 1,4 dioxane (400 mL). The flask was equipped with a reflux condenser and heated to 80° C. After 12 hours the reaction was cooled, diluted with $CH_2Cl_2$ (~200 mL), and filtered through celite. The filtrate was washed once with water and then concentrated to an oil. The crude product was purified by silica gel column chromatography (3% to 10% MeOH in $CH_2Cl_2$) to afford compound A3 (30.8 g, 91%).

MS: M+H=300

Example 2

Step A', Method A

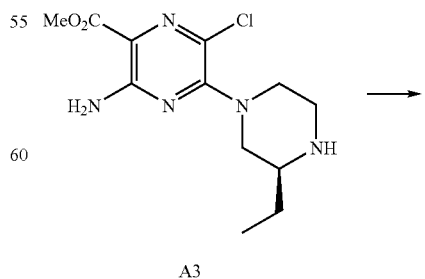

-continued

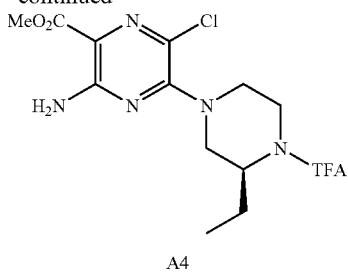

A4

A solution of A3 (19 g, 63 mmol) and triethylamine (26 mL, 189 mmol) in CH$_2$Cl$_2$ (300 mL) was treated with trifluoroacetic anhydride (13 mL, 94 mmol) at 0° C. The reaction mixture was stirred for 16 hours at 0° C. to 25° C. The reaction mixture was treated with aqueous NaHCO$_3$ solution and stirred for additional 10 hours at 25° C. The organic layers were exctracted with CH$_2$Cl$_2$ and the combined organic solution was washed with brine solution, dried (Na$_2$SO$_4$), and concentrated in vacuo. The crude product A4 (24.9 g, 100%) was pure enough to use in the next step without further purification.

MS: M+H=396

Example 3

Step B, Method A

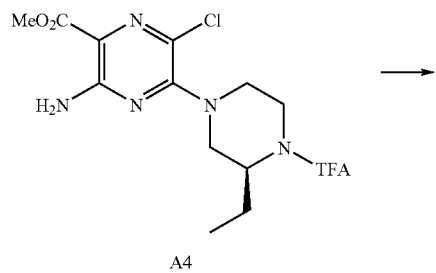

A4

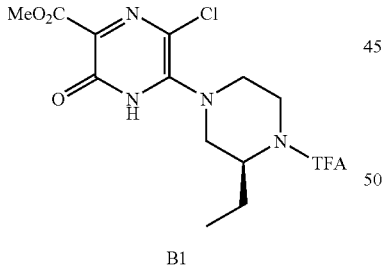

B1

A cold suspension of A4 (3.09 g, 7.8 mmol) in THF (78 mL) was treated with 50% aqueous H$_2$SO$_4$ solution (5 mL) and t-butyl nitrite (5 mL). The reaction mixture was stirred for 1 hour at 0° C. The reaction mixture was added to a mixture of CH$_2$Cl$_2$ and aqueous NaHCO$_3$ solution. The mixture was stirred for 0.5 hours and the organic layers were extracted with CH$_2$Cl$_2$. The combined organic solution was washed with brine solution, dried (Na$_2$SO$_4$), and concentrated in vacuo. The crude product of formula B1 (3 g, 95%) was used for the next step without further purification.

MS: M+H=395

Example 4

Step C, Method A

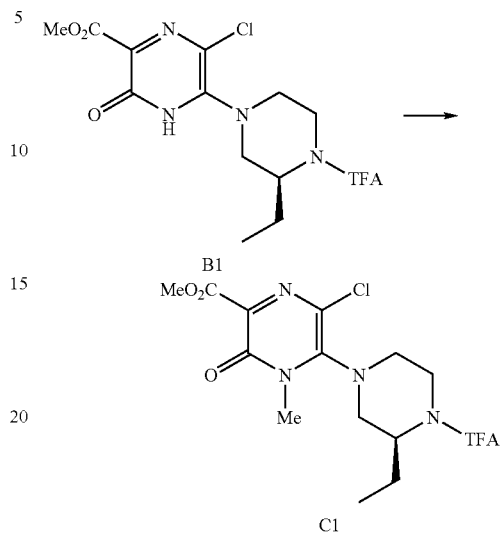

C1

A mixture of B1 (3 g, 7.8 mmol), cesium carbonate (5 g, 15.3 mmol), and methyl iodide (1.2 mL, 19.2 mmol) in acetone (180 mL) was stirred at 70° C. for 20 hours. The mixture was concentrated and the residue was dissolved in CH$_2$Cl$_2$. The organic solution was washed with water and brine solution, dried (Na$_2$SO$_4$), and concentrated in vacuo to afford the crude product of formula C1 (3.2 g, 100%).

MS: M+H=411.

Example 5

Step D, Method A

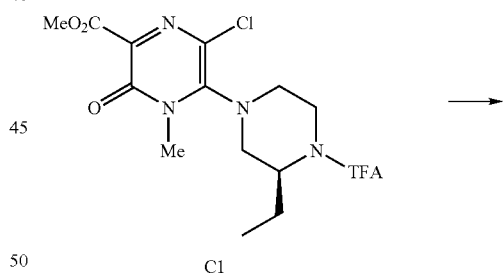

C1

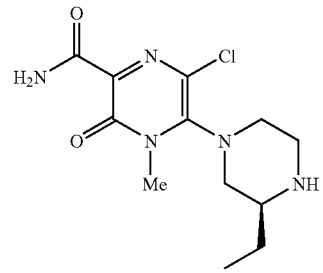

E1

A solution of C1 (238 mg, 0.58 mmol) in CH$_2$Cl$_2$ (3 mL) was treated with 7 N NH$_3$ in MeOH (1 mL) at 25° C. The reaction mixture was stirred for 4.5 hours at the temperature and then concentrated in vacuo. The residue was dissolved in 7N NH₃ in MeOH (5 mL) and the solution was stirred for 17 hours. The reaction mixture was concentrated in vacuo and the residue was purified by silica gel column chromatography (1.5% 7N NH₃-MeOH in CH₂Cl₂) to afford a compound of formula E1 (140 mg, 81%).

MS:M+H=299.

Example 6

Step F, Method A

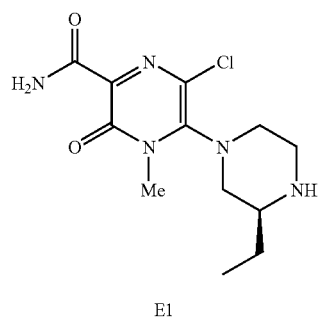

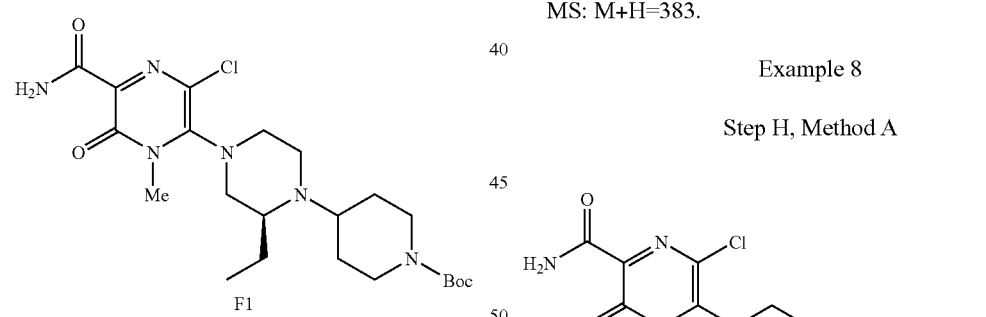

A solution of E1 (138 mg, 0.46 mmol) and N-Boc-4-piperidone (137 mg, 0.69 mmol) in 1,2-dichloroethane (4 mL) was treated with NaBH(OAc)₃ (292 mg, 1.38 mmol) at 25° C. The reaction mixture was stirred at 60° C. for 16 hours. To the mixture was added additional NaBH(OAc)₃ (60 mg, 0.28 mmol) and the reaction mixture was continued to stir at 60° C. for 3 hours. The reaction mixture was cooled and added to aqueous NaHCO₃ solution. The organic layers were extracted with EtOAc and the combined organic solution was washed with brine solution, dried (Na₂SO₄), and concentrated in vacuo. The residue was purified by silica gel column chromatography (2.5% MeOH in CH₂Cl₂) to afford F1 (105 mg, 47%).

MS: M+H=483.

Example 7

Step G, Method A

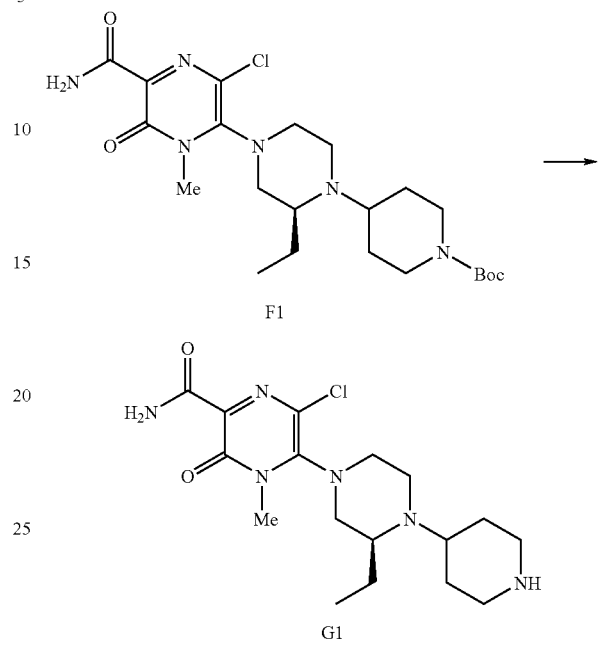

A solution of F1 (92 mg, 0.19 mmol) in CH₂Cl₂ (2 mL) was treated with trifluoroacetic acid (0.2 mL) at 0° C. The reaction mixture was stirred for 3 hours at 0° C. to 25° C. The reaction mixture was concentrated in vacuo and the residue was purified by silica gel column chromatography (2.5% to 10% 7N NH₃-MeOH in CH₂Cl₂) to afford G1 (35 mg, 48%).

MS: M+H=383.

Example 8

Step H, Method A

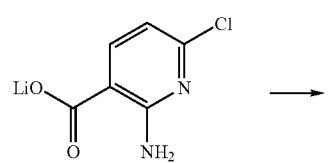

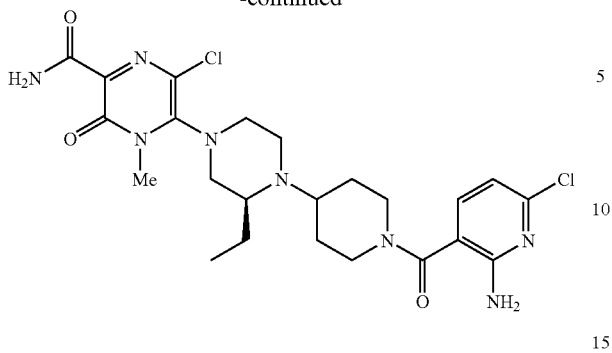

A solution of G1 (35 mg, 0.091 mmol) in DMF (1 mL) was treated with lithium 2-amino-6-chloronicotinate (19.6 mg, 0.11 mmol, preparation : see below), 1-[3-(dimethylamino)propyl]-3-ethylcarbodiimide hydrochloride (EDCl, 35 mg, 0.18 mmol), and 1-hydroxybenzotriazole (HOBt, 37 mg, 0.27 mmol) at 25° C. The reaction mixture was stirred for 24 hours at the temperature and added to aqueous NaHCO$_3$ solution. The mixture was stirred for 2 hours and the organic layers were extracted with EtOAc. The combined organic solution was washed with brine solution, dried (Na$_2$SO$_4$), and concentrated in vacuo. The residue was purified by silica gel column chromatography (1.5% 7N NH$_3$-MeOH in CH$_2$Cl$_2$) to afford H1 (26 mg, 55%).

MS: M+H=520.

Example 9

Step E', Method B

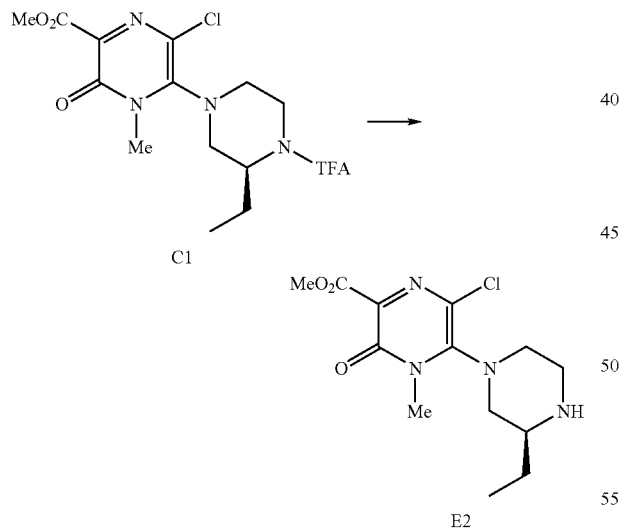

A solution of C1 (1.03 g, 2.5 mmol) in MeOH (70 mL) and water (20 mL) was treated with NaBH$_4$ (226 mg, 5.95 mmol, added as 4 portions for 23 hours) at 25° C. The reaction mixture was stirred for 24 hours at 25° C. and quenched by addition of aqueous saturated NaHCO$_3$ solution (20 mL). The mixture was stirred for 1 hour at 25° C. and the organic solvent was evaporated off. The aqueous solution was extracted with EtOAc and the combined organic solution was washed with brine solution, dried (Na$_2$SO$_4$), and concentrated in vacuo. The residue was purified by silica gel column chromatography (3% to 5% MeOH in CH$_2$Cl$_2$) to afford E2 (496 mg, 63%).

MS: M+H=315.

Example 10

Step I', Method B

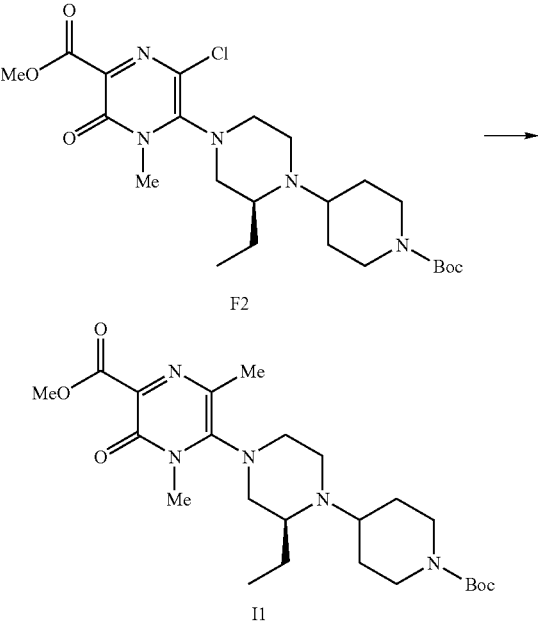

A mixture of F2 (161 mg, 0.32 mmol), methyl boronic acid (30 mg, 0.49 mmol), [1,1'-bis(diphenylphosphino)ferrocene]dichloropalladium(II), complex with dichloromethane (1:1) (52 mg, 0.064 mmol), and potassium carbonate (89 mg, 0.64 mmol) in DMF (2 mL) was degassed and stirred at 70° C. for 20 hours. The reaction mixture was cooled and added to aqueous solution of NaHCO$_3$. The organic layers were extracted with EtOAc and the combined organic solution was washed with brine solution, dried (Na$_2$SO$_4$), and concentrated in vacuo. The residue was purified by preparative TLC (10% MeOH in CH$_2$Cl$_2$) to afford I1 (115 mg, 75%).

MS: M+H=478.

Example 11

Step D', Method B

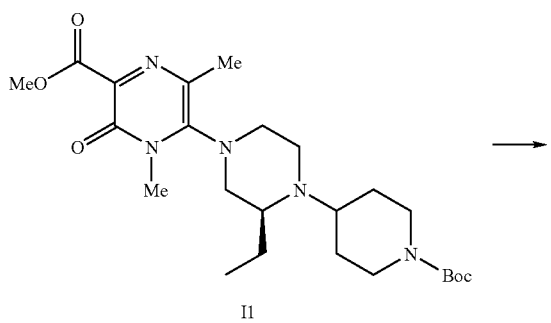

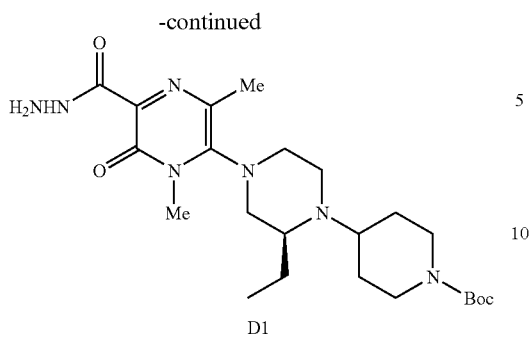

D1

A compound of structure of I1 (107 mg, 0.22 mmol) in EtOH (4 mL) was treated with hydrazine (70 μL, 2.2 mmol) and the reaction mixture was stirred at 60° C. for 16 h. The reaction mixture was concentrated in vacuo and the residue was purified by silica gel column chromatography (2.5% to 5% MeOH in CH$_2$Cl$_2$) to afford D1 (64.2 mg, 60%).
MS: M+H=478.

Example 12

Step J, Method B

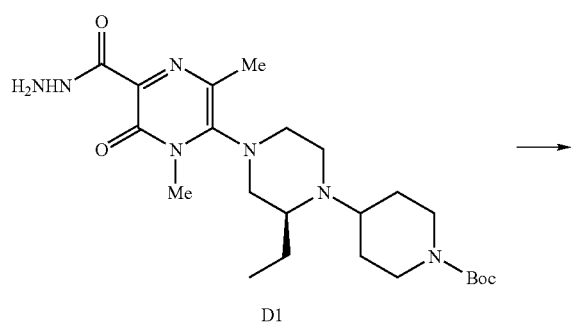

D1

⟶

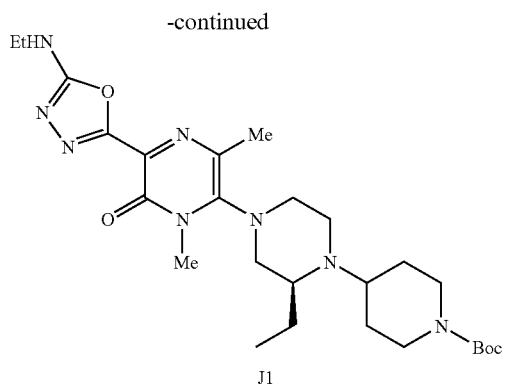

J1

A solution of compound D1 (65 mg, 0.135 mmol) in CH$_2$Cl$_2$ (2 mL) was treated with ethyl isocyanate (13 μL, 0.163 mmol) at 0° C. The reaction mixture was stirred at 25° C. for 1 hour. The reaction mixture was treated with triethylamine (94 μL, 0.675 mmol) and p-toluenesulfonyl chloride (31 mg, 0.162 mmol) at 25° C. and the mixture was stirred for 20 hours. The reaction mixture was added to aqueous solution of NaHCO$_3$ and the organic solution was extracted with CH$_2$Cl$_2$. The combined organic solution was washed with brine solution, dried (Na$_2$SO$_4$), and concentrated in vacuo. The residue was purified by preparative TLC (10% MeOH in CH$_2$Cl$_2$) to afford J1 (26 mg, 36%).
MS: M+H=531.

Example 13

Step H", Method B

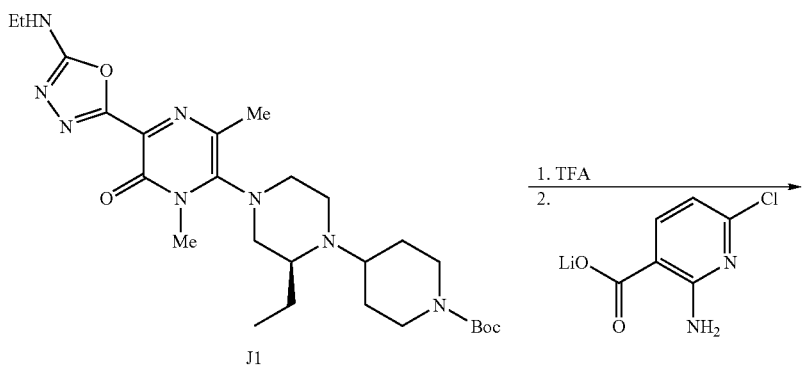

J1

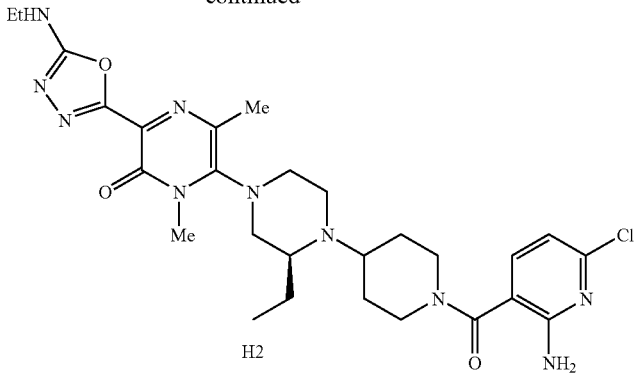

A solution of compound J1 (26 mg, 0.049 mmol) in CH$_2$Cl$_2$ (1 mL) was treated with trifluoroacetic acid (0.1 mL) at 25° C. The reaction mixture was stirred at the temperature for 1 hour. The reaction mixture was concentrated in vacuo and the residual material was dissolved in DMF (0.6 mL). The solution was treated with triethylamine (20 mL, 0.14 mmol) and the mixture was stirred for 0.25 hours before addition of lithium 2-amino-6-chloronicotinate (10.5 mg, 0.06 mmol, preparation: see below), 1-[3-(dimethylamino)propyl]-3-ethylcarbodiimide hydrochloride (EDCl, 19 mg, 0.1 mmol), and 1-hydroxybenzotriazole (HOBt, 20 mg, 0.15 mmol) at 25° C. The reaction mixture was stirred for 7 hours at 25° C. The mixture was added to an aqueous NaHCO$_3$ solution and the organic layers were extracted with EtOAc. The combined organic solution was washed with brine solution, dried (Na$_2$SO$_4$), and concentrated in vacuo. The residue was purified by preparative TLC (5% MeOH in CH$_2$Cl$_2$) to afford H2 (16.5 mg, 59%). MS: M+H=437

Example 14

Step J', Method C

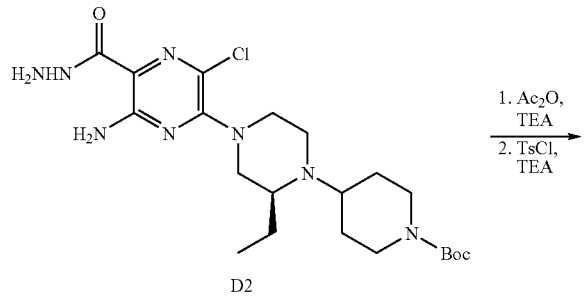

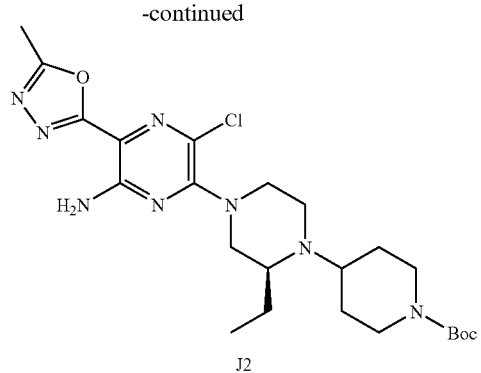

solution of compound D2 (2.26 g, 4.68 mmol) in CH$_2$Cl$_2$ (20 mL) was treated with acetic anhydride (0.58 mL, 6.08 mmol) and triethylamine (1.3 mL, 9.36 mmol) at 0° C. The reaction mixture was stirred at 25° C. for 4 hours. The reaction mixture was added to aqueous solution of NaHCO$_3$ and the organic solution was extracted with CH$_2$Cl$_2$. The combined organic solution was washed with brine solution, dried (Na$_2$SO$_4$), and concentrated in vacuo. The residue was purified by silica gel column chromatography (3% to 10% MeOH in CH$_2$Cl$_2$) to afford intermediate D3 (1.9 g, 78%). A solution of intermediate D3 (518 mg, 0.99 mmol) in CH$_2$Cl$_2$ (18 mL) was treated with p-toluenesulfonyl chloride (207 mg, 1.09 mmol) and triethylamine (0.83 mL, 5.94 mmol) at 25° C. The reaction mixture was stirred at 25 ° C. for 48 hours. The reaction mixture was added to aqueous solution of NaHCO$_3$ and the organic solution was extracted with CH$_2$Cl$_2$. The combined organic solution was washed with brine solution, dried (Na$_2$SO$_4$), and concentrated in vacuo. The residue was purified by silica gel column chromatography (2.5% 7N NH$_3$-MeOH in CH$_2$Cl$_2$) to afford compound J2 (415 mg, 83%). MS: M+H=507

Example 15

Step G', Method C

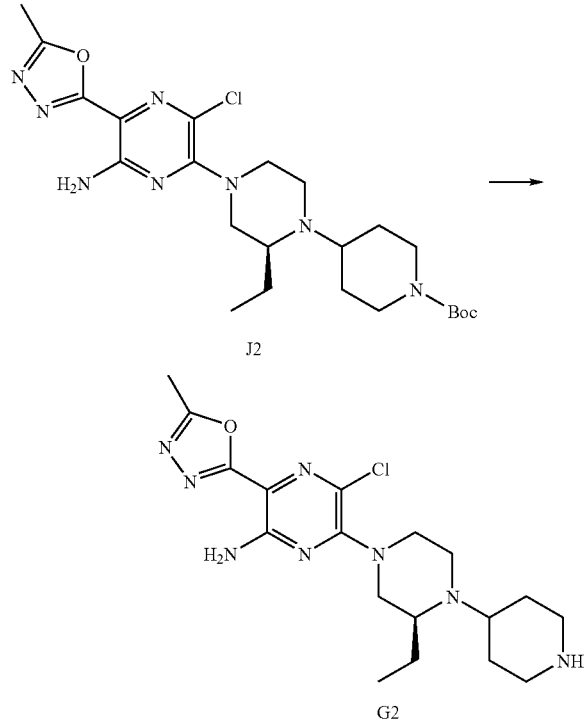

A solution of compound J2 (462 mg, 0.91 mmol) in CH$_2$Cl$_2$ (10 mL) was treated with trifluoroacetic acid (1 mL) at 25° C. The reaction mixture was stirred at the temperature for 3 hours. The reaction mixture was concentrated in vacuo and the residual material was redissolved in CH$_2$Cl$_2$ (6 mL). The solution was treated with 7N NH$_3$ in MeOH (~1 mL) and the mixture was stirred for 0.5 hours at 0° C. The mixture was concentrated in vacuo and the residue was purified by silica gel column chromatography (3% to 10% MeOH in CH$_2$Cl$_2$) to afford G2 (325 mg, 88%).

MS: M+H=407

Example 16

Step H''', Method C

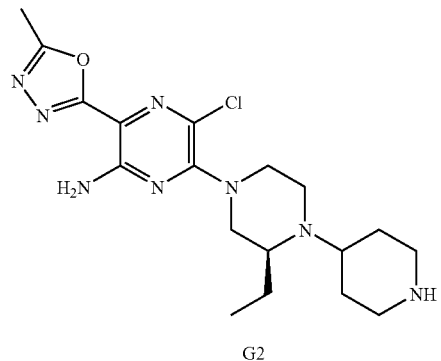

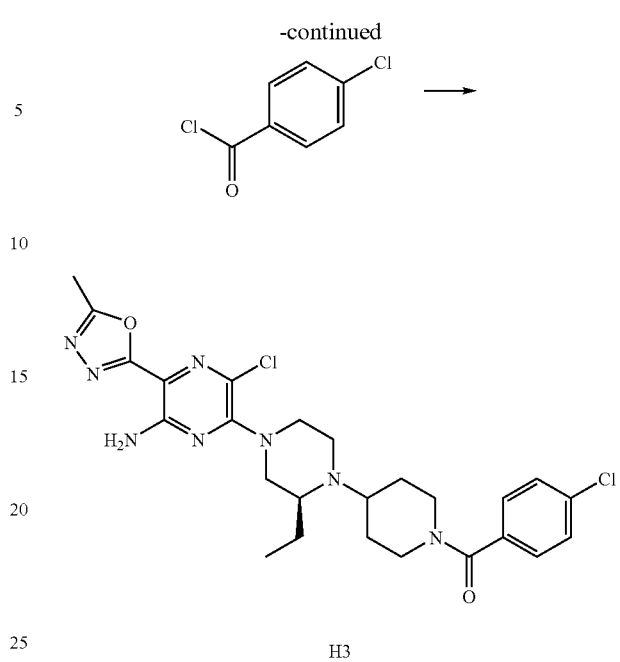

A solution of compound G2 (429 mg, 1.05 mmol) in CH$_2$Cl$_2$ (18 mL) and THF (4.5 mL) was treated with triethylamine (0.29 mL, 2.1 mmol) and 4-chlorobenzoyl chloride (0.16 mL, 1.26 mmol) at 0° C. The reaction mixture was stirred at the temperature for 1.5 hours. The reaction mixture was added to an aqueous solution of NaHCO$_3$ and the organic solution was extracted with CH$_2$Cl$_2$. The combined organic solution was washed with brine solution, dried (Na$_2$SO$_4$), and concentrated in vacuo. The residue was purified by silica gel column chromatography (1.5% to 5% MeOH in CH$_2$Cl$_2$) to afford compound H3 (565 mg, 99%).

MS: M+H=545

Example 17

Step B', Method C

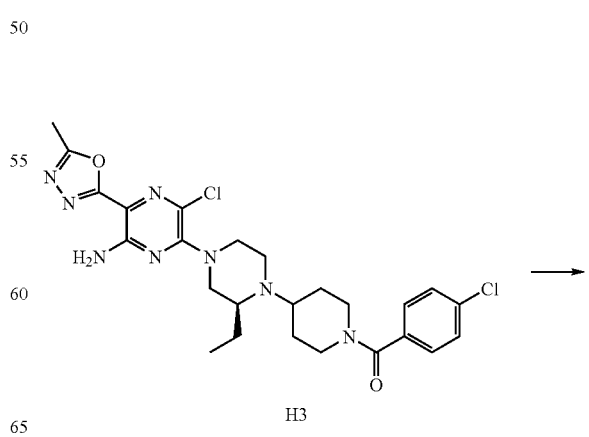

-continued

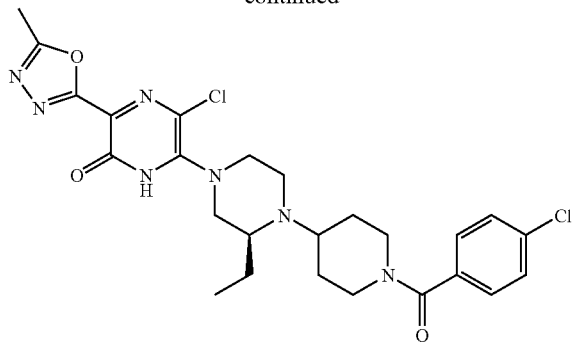

B2

A cold solution of H3 (hydrochloride salt, 23 mg, 0.039 mmol) in THF (0.5 mL) and water (0.1 mL) was treated with 50% aqueous $HBF_4$ solution (8 μL) and t-butyl nitrite (8 μL). The reaction mixture was stirred for 16 hour at 25° C. The reaction mixture was added to a mixture of $CH_2Cl_2$ and aqueous $NaHCO_3$—NaOH (5%) solution. The mixture was stirred for 0.5 hours and the organic layers were extracted with $CH_2Cl_2$. The combined organic solution was washed with brine solution, dried ($Na_2SO_4$), and concentrated in vacuo. The residue was purified by preparative TLC (5% MeOH in $CH_2Cl_2$) to afford B2 (4.3 mg, 19%).

MS: M+H=546

Lithium 2-amino-6-chloronicotinate

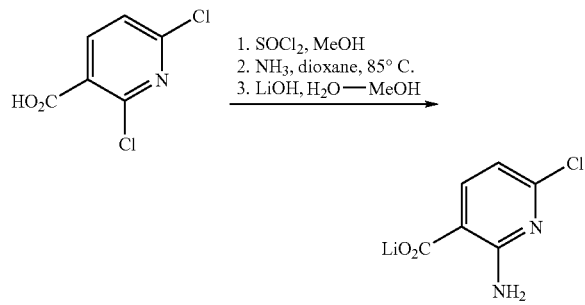

A solution of 2,6-dichloronicotinic acid (20.2 g, 0.105 mol) in MeOH (500 mL) was cooled to 0 °C. and neat thionyl chloride (38 mL, 63 g, 0.525 mol) was added over ~0.5 hours. The reaction mixture was stirred at 0° C. for 1 hour. The cooling bath was removed, the reaction temperature was allowed to warm to 25° C., and the reaction was allowed to stir for an additional 2 days at 25° C. The solvent was removed under reduced pressure to give an off-white residue. The residue was dissolved in $Et_2O$ (~500 mL) and the resulting solution was washed successively with saturated aqueous $NaHCO_3$ solution (~300 mL), water (~300 mL), and brine solution (~300 mL). The organic layer was separated, dried over anhydrous $MgSO_4$, and filtered. Removal of the solvent under reduced pressure yielded methyl 2,6-dichloronicotinate (21.0 g, 97%) as a white solid.

Performed in duplicate on identical scales in two pressure vessels, methyl 2,6-dichloronicotinate (4.5 g, 22 mmol) was dissolved in $NH_3$ solution (250 mL, 0.5 M in 1,4-dioxane; 0.125 mol). The pressure vessels were sealed and heated at (85±5) ° C. for 9 days. The two reaction mixtures were allowed to cool to 25° C., then combined and concentrated under reduced pressure to yield a white solid. Dissolution of the solid in 1:1 acetone-MeOH (~500 mL), followed by adsorption onto silica gel (25 g) and then purification by flash column chromatography (25:10:1 hexane-$CH_2Cl_2$-$Et_2O$), gave 6.08 g (75%) of methyl 2-amino-6-chloronicotinate.

A solution of $LiOH.H_2O$ (1.38 g, 33 mmol) in water (33 mL) was added in one portion to a suspension of methyl 2-amino-6-chloronicotinate (6.08 g, 27 mmol) in MeOH (110 mL). The reaction mixture was stirred at 70° C. for 24 hours, and gradually became homogeneous. The solvents were removed under reduced pressure, and after the resulting white solid was dried under vacuum (<1 mmHg) to constant weight, 5.51 g (95%) of lithium 2-amino-6-chloronicotinate was obtained.

Biological Examples

The inventive compounds can readily be evaluated to determine activity at The CXCR3 receptors by known methods, such as, for example, Development of Human CXCR3 (N-delta 4) Binding Assay.

Cloning and Expression of Human CXCR3 (N-delta 4):

The DNA encoding human CXCR3 was cloned by PCR using human genomic DNA (Promega, Madison, Wis.) as a template. The PCR primers were designed based on the published sequence of human orphan receptor GPR9 (1) with incorporated restriction sites, a Kozak consensus sequence, CD8 leader and Flag tag. The PCR product was subcloned into the mammalian expression vector pME18Sneo, a derivative of the SR-alpha expression vector (designated as pME18Sneo-hCXCR3 (N-delta 4).

IL-3-dependent mouse pro-B cells Ba/F3 were transfected by electroporation in 0.4 ml Dulbecco's PBS containing $4\times10^6$ cells with 20 μg of pME18Sneo-hCXCR3 (N-delta 4) plasmid DNA. Cells were pulsed at 400 Volts, 100 OHMs, 960 μFd. The transfected cells were under selection with 1 mg/ml G418 (Life Technologies, Gaithersburg, Md.). G418-resistant Ba/F3 clones were screened for CXCR3 expression by specific binding of [$^{125}$I] IP-10 (NEN Life Science Products, Boston, Mass.).

Preparation of Ba/F3-hCXCR3 (N-delta 4) membranes:

Ba/F3 cells expressing human CXCR3 (N-delta 4) were pelleted and resuspended in the lysis buffer containing 10 mM HEPES, pH 7.5 and Complete® protease inhibitors (1 tablet per 100 ml) (Boehringer Mannheim, Indianapolis, Ind.) at a cell density of $20\times10^6$ cells per ml. After 5 minutes incubation on ice, cells were transferred to 4639 cell disruption bomb (Parr Instrument, Moline, Ill.) and applied with 1,500 psi of nitrogen for 30 minutes on ice. Large cellular debris was removed by centrifugation at 1,000×g. Cell membrane in the supernatant was sedimented at 100,000×g. The membrane was resuspended in the lysis buffer supplemented with 10% sucrose and stored at −80° C. Total protein concentration of the membrane was determined by BCA method from Pierce (Rockford, Ill.).

Human CXCR3 (N-delta 4) Scintillation Proximity Assay (SPA):

For each assay point, 2 μg of membrane was preincubated for 1 hr with 300 μg wheat germ agglutinin (WGA) coated SPA beads (Amersham, Arlington Heights, Ill.) in the binding buffer (50 mM HEPES, 1 mM $CaCl_2$, 5 mM $MgCl_2$, 125 mM NaCl, 0.002% $NaN_3$, 1.0% BSA) at room temperature. The beads were spun down, washed once, resuspended in the binding buffer and transferred to a 96-well Isoplate (Wallac, Gaithersburg, Md.). 25 pM of [$^{125}$I] IP-10 with tested compounds in a series of titration were added to start the reaction.

After 3 hr reaction at room temperature, the amount of [$^{125}$I] IP-10 bound to the SPA beads was determined with a Wallac 1450 Microbeta counter.

The Ki values for the various example compounds of the present invention are given in the afore-mentioned Table 1. From these values, it would be apparent to the skilled artisan that the compounds of the invention have excellent utility CXCR3 antagonists.

While the present invention has been describe in conjunction with the specific embodiments set forth above, many alternatives, modifications and variations thereof will be apparent to those of ordinary skill in the art. All such alternatives, medications and variations are intended to fall within the spirit and scope of the present invention.

What is claimed is:

1. A compound having the structure shown in Formula 1:

Formula 1

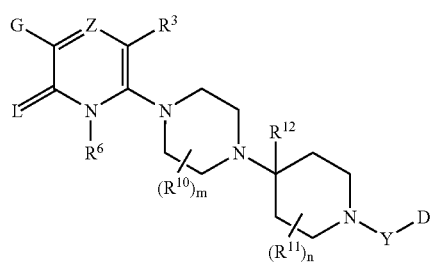

or a pharmaceutically acceptable salt thereof, wherein:

G is selected from the group consisting of H$_2$N(C=O)— and a 5-membered heteroaryl or heterocyclenyl ring, said 5-membered heteroaryl or heterocyclenyl ring is selected from the group consisiting of dihydroimidazole, imidazole, dihydrooxazole, oxazole, dihydrooxadiazole, oxadiazole, triazole, and tetrazole, and wherein said heteroaryl or heterocyclenyl ring can be either (i) unsubstituted, or (ii) optionally independently substituted on one or more ring carbon atoms with one or more $R^9$ substituents, L is O;

Z is N;

$R^3$ is H, alkyl, —CN, haloalkyl or halogen;

$R^6$ is selected from the group consisting of H, alkyl, arylalkyl, and alkylaryl;

the $R^9$ moieties can be the same or different, each being independently selected from the group consisting of H, —CF$_3$, —CH$_2$CH$_2$OH, —CH$_2$CH$_2$NH$_2$, —NH$_2$, —NHCH$_3$, —N(H)CH$_2$CH$_3$, —N(H)CH(CH$_3$)$_2$, —N(H)CH$_2$CH$_2$CH$_3$, —N(H)CH$_2$C(=O)OCH$_3$, and —N(H)CH$_2$CH$_2$OH;

the $R^{10}$ moieties can be the same or different, each being independently selected from the group consisting of H and alkyl;

the $R^{11}$ moieties can be the same or different, each being independently selected from the group consisting of H and alkyl;

$R^{12}$ is H or alkyl;

ring D is a six membered aryl or heteroaryl ring having 0-4 N heteroatoms, wherein ring D is unsubstituted or optionally substituted with 1-5 independently selected $R^{20}$ moieties;

the $R^{20}$ moieties can be the same or different, each being independently selected from the group consisting of H, alkyl, halogen, and amino, Y is selected from the group consisting of —CH$_2$— and —C(=O)—;

m is 0 to 2;

n is 0 to 2.

2. The compound according to claim 1, wherein G is

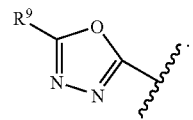

3. The compound according to claim 1, wherein $R^3$ is selected from the group consisting of H, —Cl and —CH$_3$.

4. The compound according to claim 1, wherein the $R^9$ moiety is selected from the group consisting of —NH$_2$ and —N(H)CH$_2$CH$_3$.

5. The compound according to claim 1, wherein $R^{10}$ is alkyl.

6. The compound according to claim 5, wherein said alkyl is selected from the group consisting of —CH$_3$, —CH$_2$CH$_3$ and —CH$_2$CH$_2$CH$_3$.

7. The compound according to claim 6, wherein $R^{10}$ is —CH$_2$CH$_3$ and m is 1.

8. The compound according to claim 1, wherein ring D is substituted by 1-4 $R^{20}$ moieties.

9. The compound according to claim 1, wherein said aryl ring of D is phenyl and said heteroaryl ring of D is pyridyl.

10. The compound according to claim 1, wherein m is 1.

11. The compound according to claim 1, wherein G is selected independently from the group consisting of H$_2$N(C=O)— and

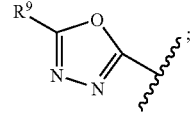

$R^3$ is selected from the group consisting of H, —Cl and —CH$_3$;

$R^9$ is selected from the group consisting of H, —Cl and —CH$_3$;

$R^{10}$ is —CH$_2$CH$_3$;

$R^{11}$ is H;

$R^{12}$ is H;

ring D is a 6 membered aryl, or heteroaryl ring and substituted by 1-4 $R^{20}$ moieties;

$R^{20}$ moieties can be the same or different, each being independently selected from the group consisting of H, halogen, and amino;

Y is selected from the group consisting of: —CH$_2$—, and —C(=O)—;

m is 1; and n is 0.

12. A compound selected from the group consisting of the following:

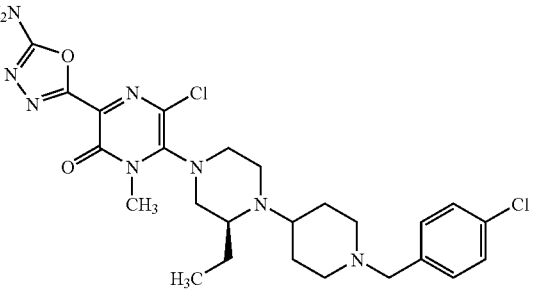

71
-continued
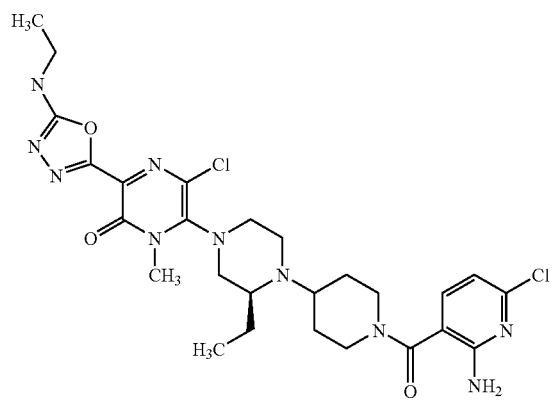
72
-continued
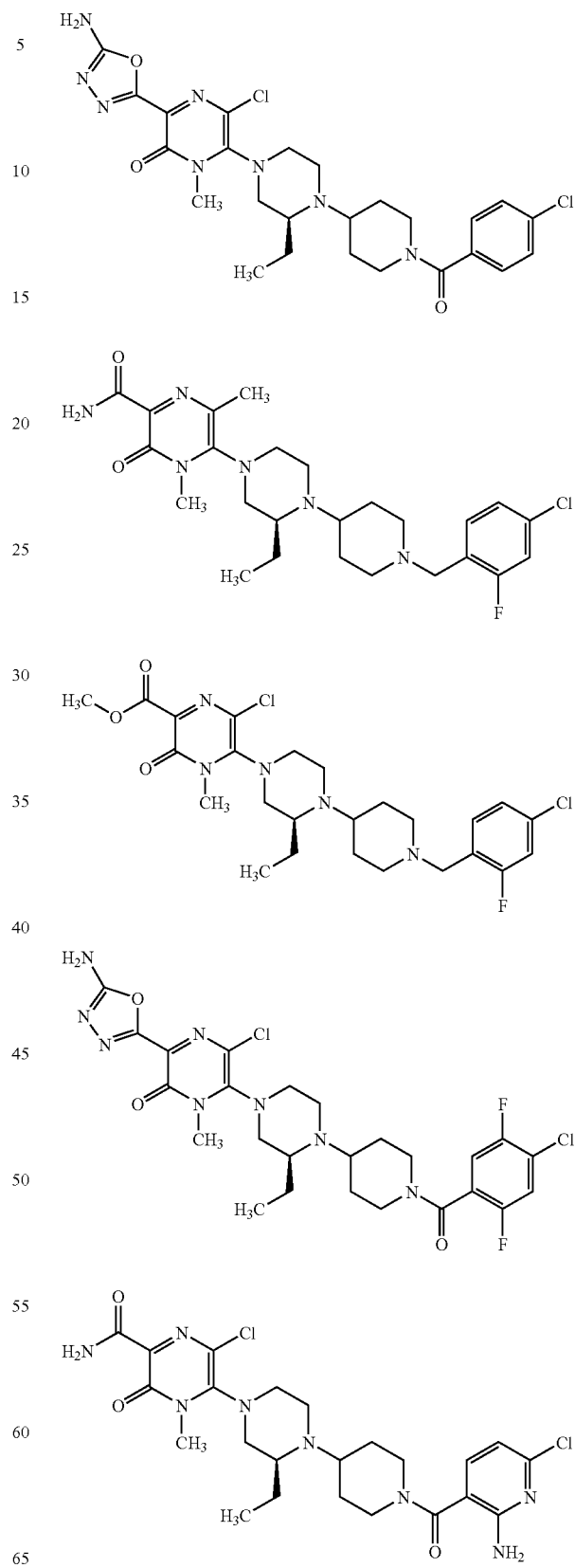

-continued

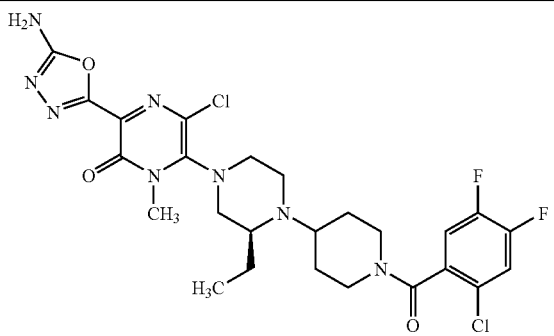

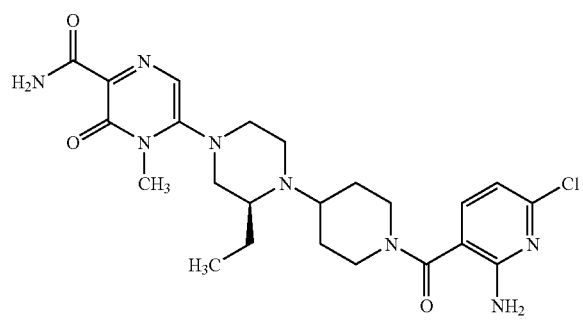

or a pharmaceutically acceptable salt thereof.

13. A compound according to claim 12, wherein the compound is selected from the group consisting of

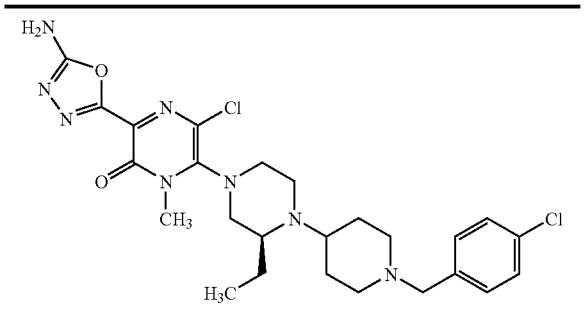

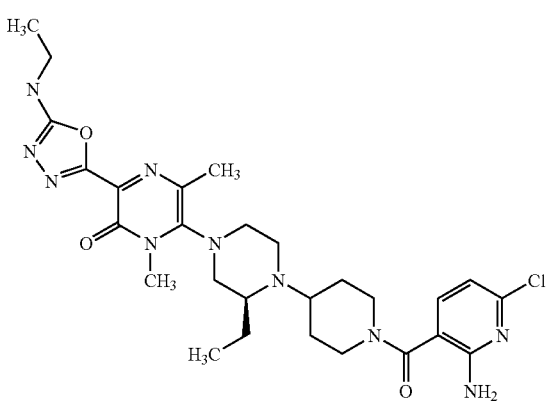

-continued

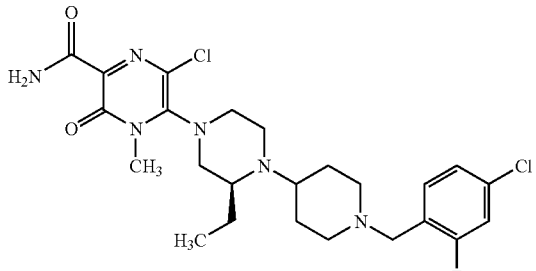

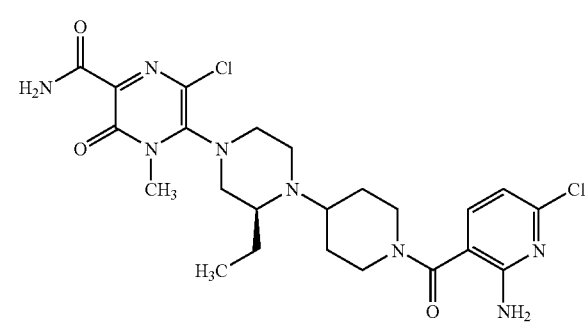

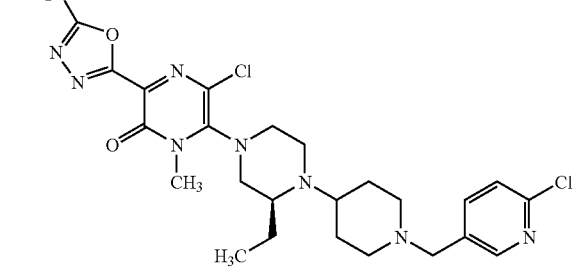

or a pharmaceutically acceptable salt thereof.

14. A compound according to claim 1 in purified form.

15. A pharmaceutical composition comprising at least one compound of claim 1, or a pharmaceutically acceptable salt thereof, in combination with at least one pharmaceutically acceptable carrier.

\* \* \* \* \*